(12) United States Patent
Yamaguchi et al.

(10) Patent No.: US 12,412,299 B2
(45) Date of Patent: Sep. 9, 2025

(54) INFORMATION PROCESSING DEVICE, INFORMATION PROCESSING METHOD, AND PROGRAM

(71) Applicant: SONY GROUP CORPORATION, Tokyo (JP)

(72) Inventors: Yuya Yamaguchi, Tokyo (JP); Takaaki Kato, Kanagawa (JP); Jun Gomita, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 380 days.

(21) Appl. No.: 17/927,487

(22) PCT Filed: May 28, 2021

(86) PCT No.: PCT/JP2021/020353
§ 371 (c)(1),
(2) Date: Nov. 23, 2022

(87) PCT Pub. No.: WO2021/251171
PCT Pub. Date: Dec. 16, 2021

(65) Prior Publication Data
US 2023/0245340 A1    Aug. 3, 2023

(30) Foreign Application Priority Data

Jun. 12, 2020    (JP) ................................ 2020-102548

(51) Int. Cl.
*G06T 7/73*    (2017.01)
*G06T 7/246*    (2017.01)

(52) U.S. Cl.
CPC ................ *G06T 7/73* (2017.01); *G06T 7/246* (2017.01); *G06T 2207/30196* (2013.01)

(58) Field of Classification Search
None
See application file for complete search history.

(56) References Cited

U.S. PATENT DOCUMENTS

| 2007/0265741 | A1* | 11/2007 | Oi | ........................ G01C 21/12 701/527 |
| 2020/0033937 | A1* | 1/2020 | Erivantcev | .............. G06T 7/246 |
| 2023/0245340 | A1* | 8/2023 | Yamaguchi | ............... G06T 7/75 382/103 |

FOREIGN PATENT DOCUMENTS

| JP | 2007-303886 A |  | 11/2007 |
| JP | 2012068772 A | * | 4/2012 |

(Continued)

OTHER PUBLICATIONS

Filippeschi et al., Survey of Motion Tracking Methods Based on Inertial Sensors: A Focus on Upper Limb Human Motion, MDPI, 2017, pp. 1-40.

*Primary Examiner* — Delomia L Gilliard
(74) *Attorney, Agent, or Firm* — Paratus Law Group, PLLC

(57) ABSTRACT

There is provided an information processing device, an information processing method, and a program that improve detection accuracy in detecting a motion or posture of a person or an object using an inertial sensor. A posture of a measurement target is estimated based on a position and orientation of each of a plurality of measurement devices arranged at a plurality of parts of the measurement target and based on a connection relationship between the measurement devices that is set based on positions and orientations of the measurement devices, each measurement device including an inertial sensor. The present technology can be applied to a motion capture system.

19 Claims, 15 Drawing Sheets

(56) References Cited

FOREIGN PATENT DOCUMENTS

| | | | | |
|---|---|---|---|---|
| JP | 2020013560 A | * | 1/2020 | ................ G06T 7/73 |
| WO | WO-2020070928 A1 | * | 4/2020 | ............ A63F 13/212 |

* cited by examiner

INFORMATION PROCESSING DEVICE, INFORMATION PROCESSING METHOD, AND PROGRAM

CROSS REFERENCE TO PRIOR APPLICATION

This application is a National Stage Patent Application of PCT International Patent Application No. PCT/JP2021/020353 (filed on May 28, 2021) under 35 U.S.C. § 371, which claims priority to Japanese Patent Application No. 2020-102548 (filed on Jun. 12, 2020), which are all hereby incorporated by reference in their entirety.

TECHNICAL FIELD

The present technology relates to an information processing device, an information processing method, and a program, and more particular, to an information processing device, an information processing method, and a program that improve detection accuracy in detecting a motion or posture of a person or an object using an inertial sensor.

BACKGROUND ART

NPL 1 discloses an inertial measurement unit (IMU) and a motion capture system that combines the IMU and a marker to detect, human motion.

CITATION LIST

Non Patent Literature

[NPL 1]
A. Filippeschi, N. Schmitz, M. Miezal, Bleser, E. Ruffaldi, and D. Stricker, "Survey of Motion Tracking Methods Based on Inertial Sensors: A Focus on Upper Limb Human Motion," In: Sensors 17.6 (2017), p. 1257.

SUMMARY

Technical Problem

There is a demand for improving detection accuracy in detecting a motion or posture of a person or object using an inertial sensor.

The present technology has been made in view of such circumstances, and aims to improve detection accuracy in detecting a motion or posture of a person or an object using an inertial sensor.

Solution to Problem

An information processing device or a program according to the present technology is an information processing device including a posture estimation unit that estimates a posture of a measurement target based on a position and orientation of each of a plurality of measurement devices arranged at a plurality of parts of the measurement target and based on a connection relationship between the measurement devices that is set based on positions and orientations of the measurement devices, each measurement device including an inertial sensor, or a program for causing a computer to function as such an information processing device.

An information processing method according to the present technology is an information processing method including, by a posture estimation unit of an information processing device, estimating a posture of a measurement target based on a position and orientation of each of a plurality of measurement devices arranged at a plurality of parts of the measurement target and based on a connection relationship between the measurement devices that is set based on positions and orientations of the measurement devices, each measurement device including an inertial sensor.

According to the present technology, a posture of a measurement target is estimated based on a position and orientation of each of a plurality of measurement devices arranged at a plurality of parts of the measurement target and based on a connection relationship between the measurement devices that is set based on positions and orientations of the measurement devices, each measurement device including an inertial sensor.

DESCRIPTION OF EMBODIMENTS

Figure 1:
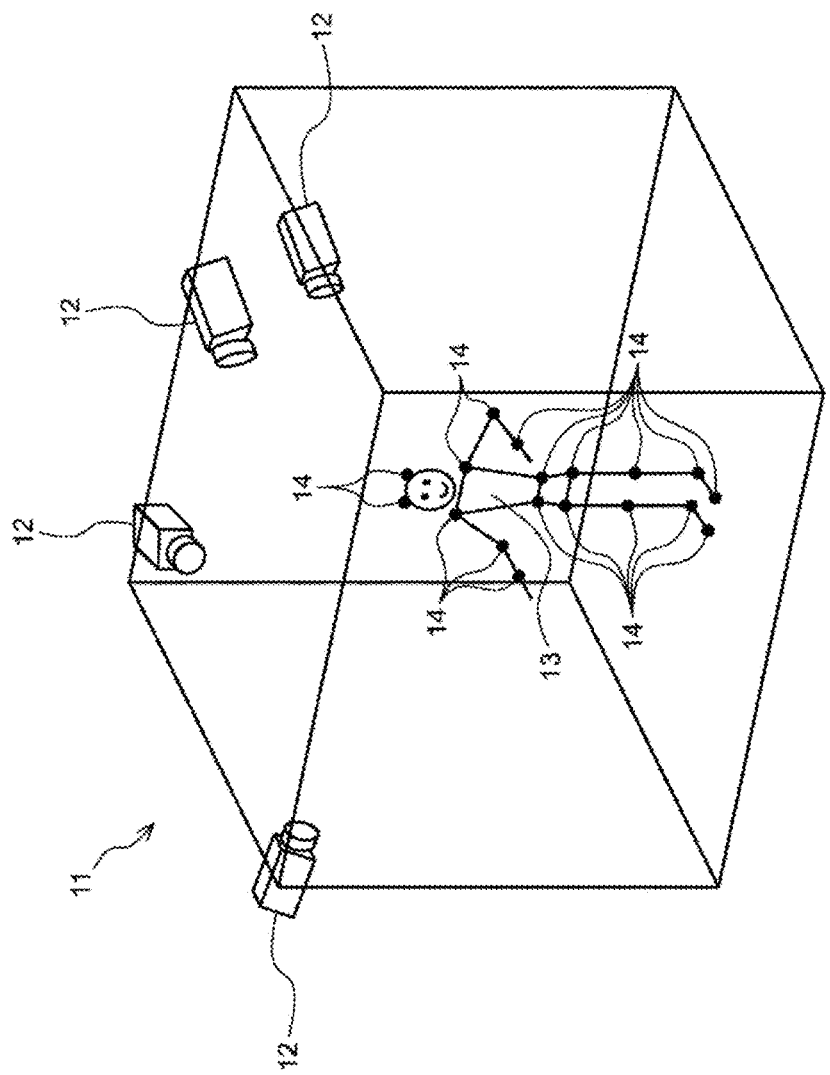
FIG. 1 is an explanatory diagram for explaining an optical motion capture system.

Hereinafter, embodiments of the present technology will be described with reference to the drawings.
<<Well-Known Motion Capture System>>
<Optical Type>
FIG. 1 is an explanatory diagram for explaining an optical motion capture system.

A motion capture system 11 in FIG. 1 includes a plurality of infrared cameras 12 installed in a studio. Reflective markers 14 that reflect infrared light are attached to the joints, head, or the like of a subject person 13 whose motion is to be captured. The infrared cameras 12 projects infrared light onto the subject person 13 to capture images of the reflective markers 14. With this configuration, the positions of the reflective markers 14 are tracked by the images captured by the infrared cameras 12, so that the motion of the subject person 13 is acquired. In this motion capture system 11, it is necessary to install a plurality of infrared cameras so as to surround the subject person 13 in order to acquire all the reflective markers. Therefore, there are drawbacks such as high cost and time and effort required for setting up the system.

<Image Recognition Type>

Figure 2:
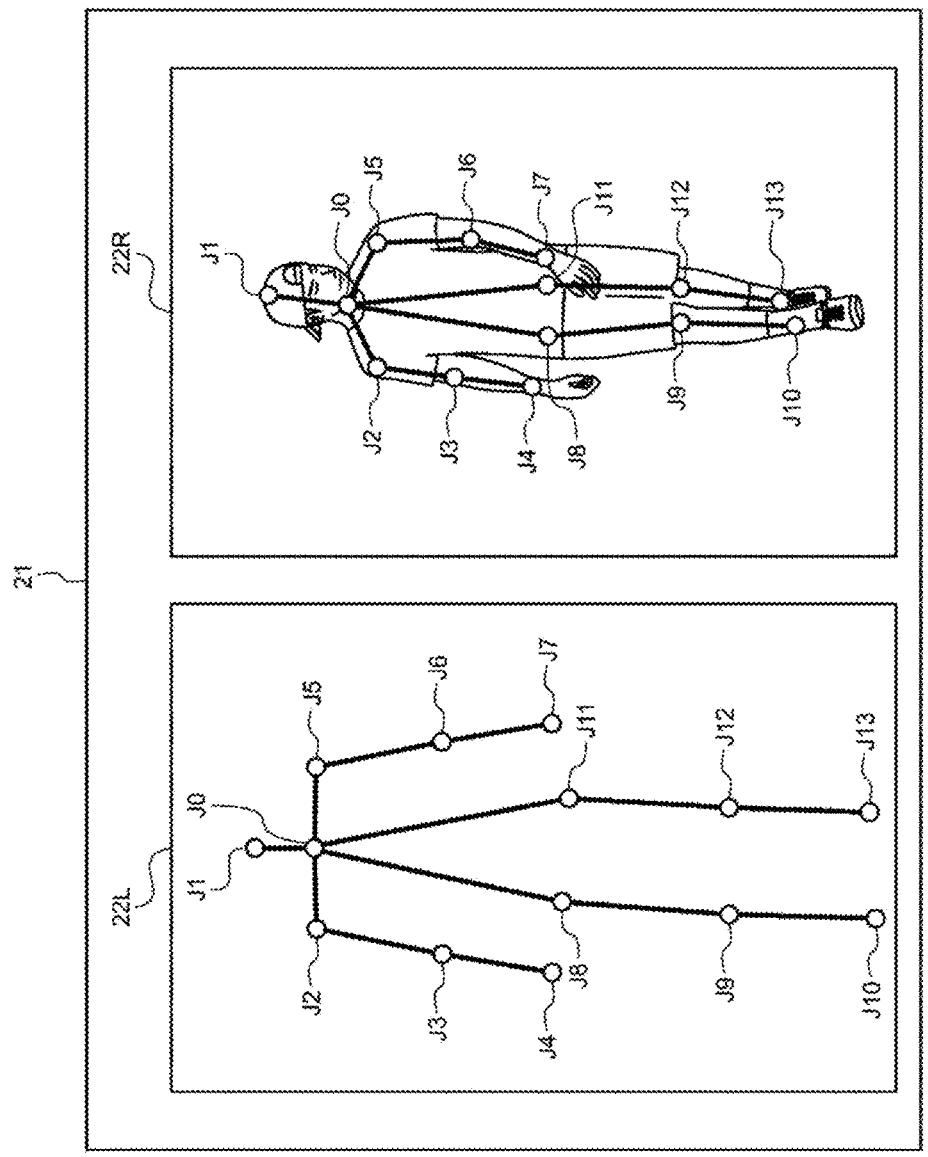
FIG. 2 is an explanatory diagram for explaining a type of motion capture system using image recognition.

FIG. 2 is an explanatory diagram for explaining a type of motion capture system, using image recognition.

In a motion capture system 21 of FIG. 2, a human body is decomposed into skeletons that connect parts such as the head, neck, shoulders, elbows, wrists, waists, knees, and ankles, as in a skeleton configuration example 22L. Also in the motion capture system 21, image recognition using deep learning or the like is performed on an image 22R of a subject person captured by one camera. As a result of the image recognition, the positions of the parts of the subject person corresponding to parts J0 to J13 of the skeleton configuration example 22L are identified or estimated.

This motion capture system 21 have drawbacks, such as learning required in advance, false detection occurring due to a difference in appearance from the time of learning, occlusion occurring, and always capturing the subject person with a camera.

<Type Using Inertial Sensor>

Figure 3:
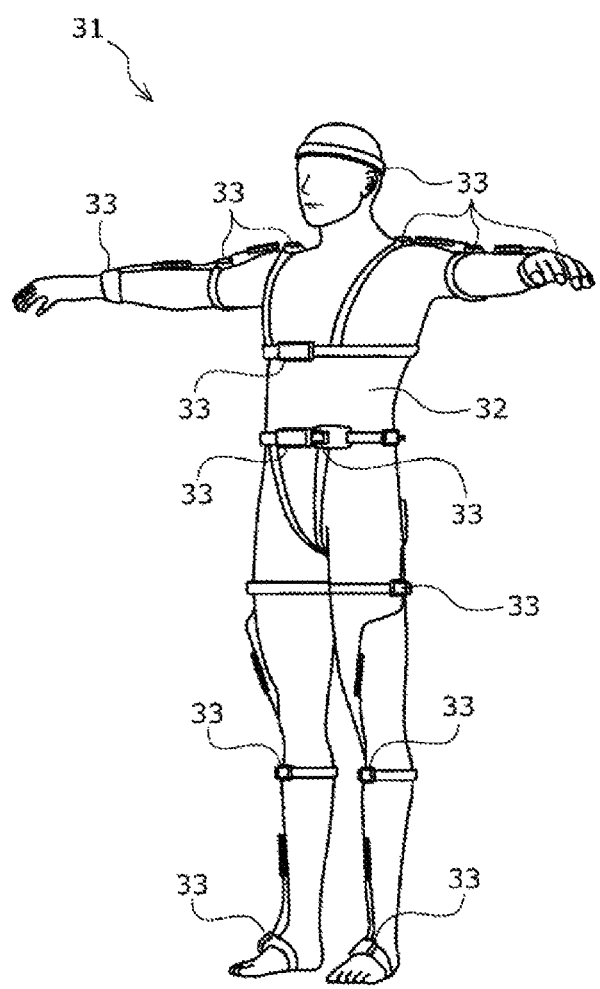
FIG. 3 is an explanatory diagram for explaining a type of motion capture system using an inertial sensor.

FIG. 3 is an explanatory diagram for explaining a type of motion capture system using an inertial sensor.

In a motion capture system 31 of FIG. 3, IMUs, which are inertial sensors, are attached to parts of the subject person whose motion is to be captured. Then, the positions and postures of the parts of the subject person are detected from pieces of sensor data obtained from the IMUs at the parts of the subject person. This motion capture system 31 reduces the drawbacks of the motion capture system 11 of FIG. 1 and the motion capture system 21 of FIG. 2.

By contrast, the motion capture system 31 of FIG. 3 has a drawback of low degree of freedom, for example, restricted motion of the subject person due to the predetermined positions at which the IMUs are attached on the subject person. In addition, it has a drawback that sufficient accuracy cannot be expected because motion capture (posture detection) using only the IMUs fails to fully control the biases (drifts) inherent in the IMUs.

A motion capture system that combines inertial sensors and reflective markers has also been proposed (for example, NPL 1).

However, the problems of the IMUs and the reflective markers as described above have not yet been solved.

In the technical fields of augmented reality (AR) and virtual reality (VR), devices have been developed that combine images and IMUS to estimate the position and posture of the users head. However, from the viewpoint of power consumption and camera size, it is not suitable as a motion capture system for a person or an object with multiple joints that move individually. It is also difficult to deal with occlusion occurring. In addition, in order to estimate the positions and postures of related joints, mutual information exchange is required, resulting in a problem that, as the number of joints increases, the amount of information to be handled and processed by the IMUs attached to the joints becomes enormous, which is difficult to achieve.

The present technology solves such problems.

<<Motion Capture System to which Present Technology is Applied>>

Figure 4:
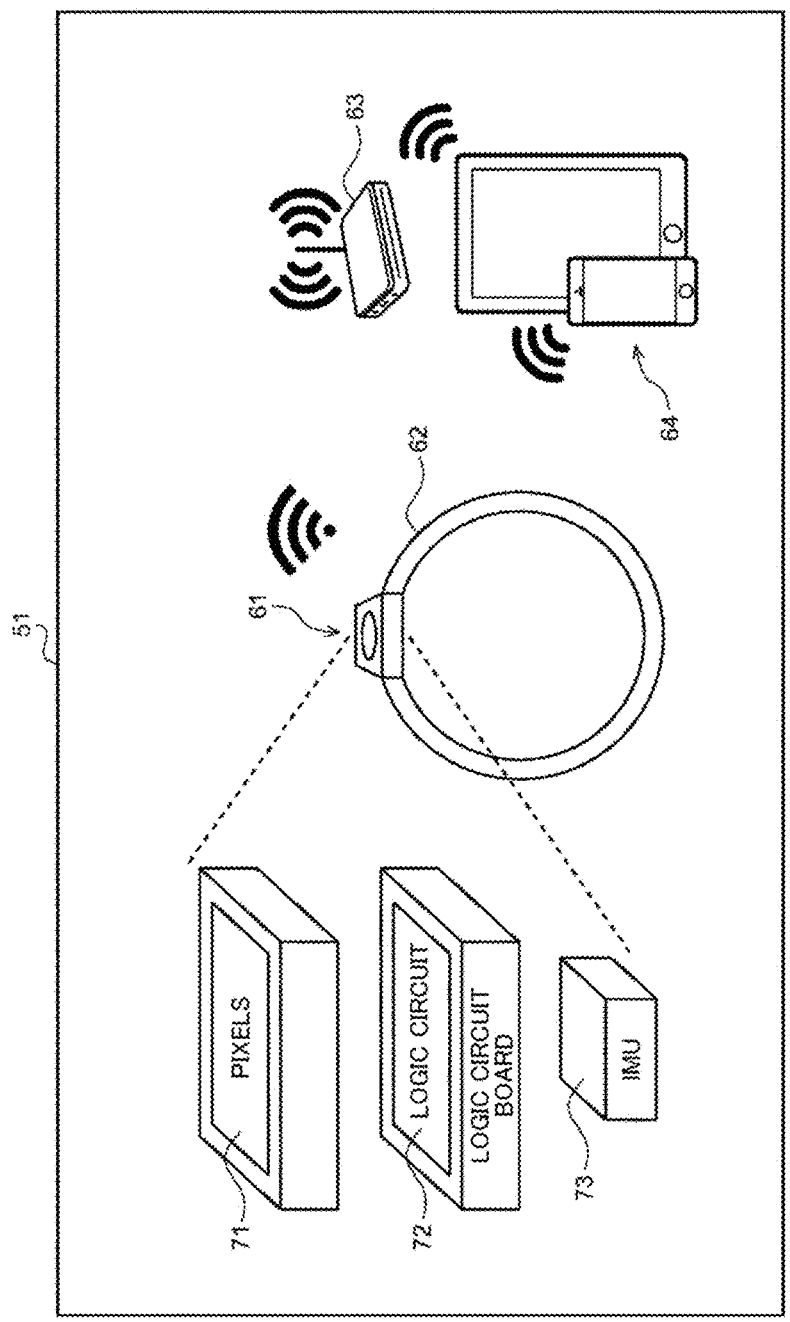
FIG. 4 is an overall diagram illustrating a configuration example of a motion capture system to which the present technology is applied.

FIG. 4 is an overall diagram illustrating a configuration example of a motion capture system to which the present technology is applied. Note that in the present embodiment, the system to which the present technology is applied is a motion capture system, but it may be a posture estimation system that estimates (detects) the posture of a person or the like.

A motion capture system 51 in FIG. 4 includes a measurement device 61, a communication device 63, and an information processing device 64.

(Measurement Device 61)

Measurement devices 61 are each attached to any one of a plurality of parts of the subject person whose motion is to be captured by means of an attachment member 62. The attachment member 62 holds the measurement device 61 and is detachably mounted in a ring shape on any one of the parts of the human body such as the head, neck, shoulders, elbows, wrists, waists, knees, and ankles. However, the attachment member 62 may have any form. The part on which the measurement device 61 is to be mounted is not limited to a specific part. The target whose motion is to be captured (measurement target) may be an object instead of a person.

The measurement device 61 includes an image sensor 71, a logic circuit board 72, and an IMU 73.

The image sensor 71, the logic circuit board 72, and the IMU 73 are integrated in, for example, a package. An optical member (such as a lens) (not illustrated) is installed on the light receiving surface side of the image sensor 71. The optical member collects light from a subject and forms an image of the subject on the light receiving surface.

The image sensor 71 photoelectrically converts the image (optical image) formed on the light receiving surface to acquire an electric signal. The image sensor 71 supplies the acquired image to a processing circuit of the logic circuit board 72. The image acquired (captured) by the image sensor 71 may be a still image for one frame, or may be a moving image composed of continuous frames. In this specification, the latter case will be described as an example.

The logic circuit board 72 includes a processing circuit that performs processing described later on images from the image sensor 71 and sensor data from the IMU 73. The logic circuit board 72 includes a communication circuit that controls communication with an external device. The communication circuit exchanges various types of data with the communication device 63 through wireless communication conforming to the Wi-Fi (registered trademark) standard, for example. Note that exchange of various types of data between the measurement device 61 and the communication device 63 is not limited to a specific form.

The IMU 73 detects the acceleration in the directions of three orthogonal axes and the angular velocity about the three orthogonal axes generated in the IMU 73 itself, and supplies them as sensor data to the processing circuit of the logic circuit board 72. A three-dimensional coordinate system set in the IMU 73 is referred to as a local coordinate system. The acceleration in the directions of three orthogonal axes and the angular velocity about the three orthogonal axes are referred to as the 3-orthogonal-axis acceleration and the 3-orthogonal-axis angular velocity, respectively.

(Communication Device 63)

The communication device 63 relays transmission of various types of data between the measurement device 61 and the information processing device 64.

The communication device 63 controls communication with the measurement device 61 (the communication circuit of the logic circuit board 72) and communication with the information processing device 64. The communication device 63 exchanges various types of data with the communication circuit of the measurement device 61 through, for example, wireless communication confirming to the Wi-Fi (registered trademark) standard. The communication device 63 exchanges various types of data with the information processing device 64 through, for example, wireless communication conforming to the Wi-Fi (registered trademark) standard. The communication device 63 transfers data from the measurement device 61 to the information processing device 64 or transfers data from the information processing device 64 to the measurement device 61.

Exchange of various types of data between the communication device 63 and the measurement device 61 and between the measurement device 61 and the information processing device 64 is not limited to a specific method. Direct communication between the measurement device 61 and the information processing device 64 may eliminate the need for the communication device 63.

(Information Processing Device 64)

The information processing device 64 acquires, via the communication device 63, various types of data from the measurement devices 61 attached to the parts of the subject person whose motion is to be captured. The information processing device 64 highly accurately calculates pose data (pose information) representing the overall posture of the subject person based on the acquired various types of data. The information processing device 64 may be any device having an arithmetic processing function of, for example, a personal computer, a doublet terminal, a smart phone, a mobile terminal, or the like.

<Functional Configuration of Measurement Device 61>

Figure 5:
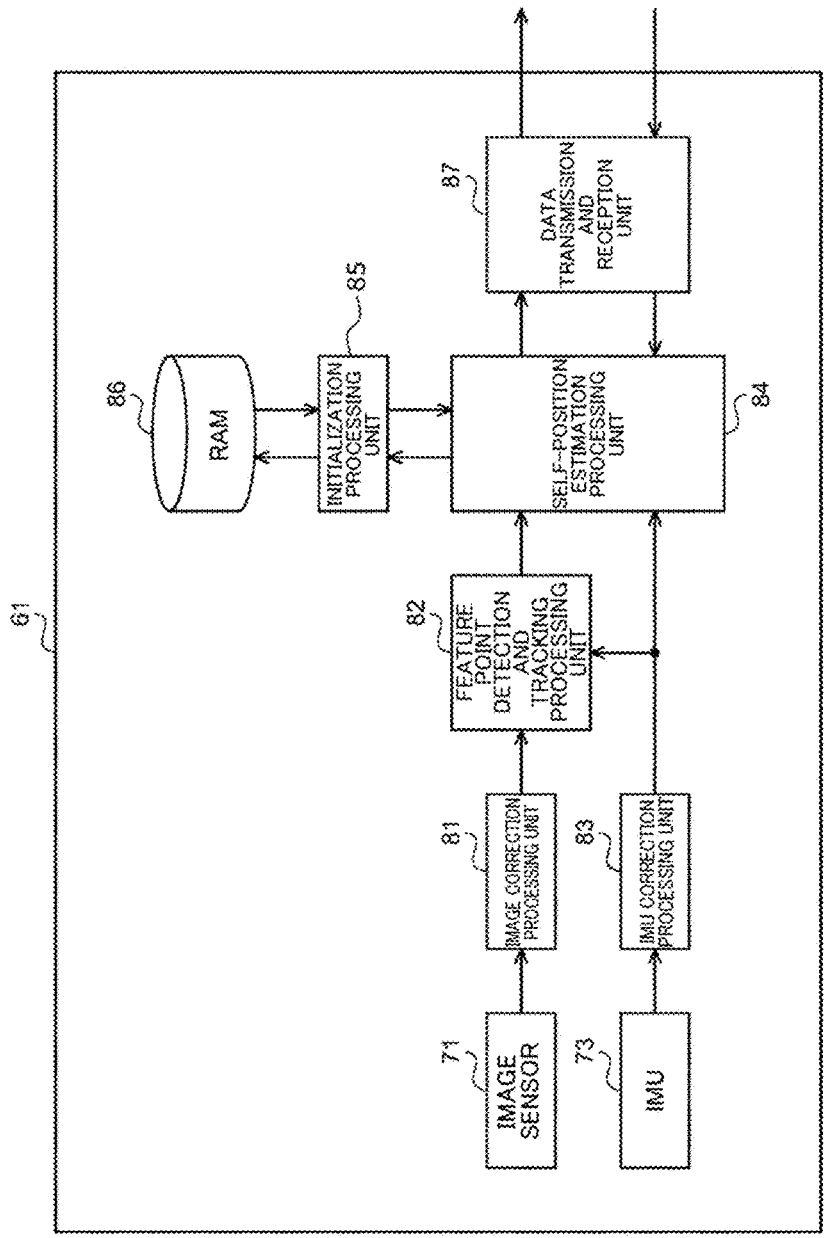
FIG. 5 is a block diagram illustrating a functional configuration of a measurement device of FIG. 4.

FIG. 5 is a block diagram illustrating a functional configuration of the measurement device 61 of FIG. 4.

The measurement device 61 includes the image sensor 71, the IMU 73, an image correction processing unit 81, a feature point detection and tracking processing unit 82, an IMU correction processing unit 83, a self-position estimation processing unit 84, an initialization processing unit 85, a RAM 86, and a data transmission and reception unit 87. The image correction processing unit 81, the feature point detection and tracking processing unit 82, the IMU correction processing unit 83, the self-position estimation processing unit 84, the initialization processing unit 85, the RAM 86, and the data transmission and reception unit 87 are components implemented by the processing circuit of the logic circuit board 72 of FIG. 4.

The image sensor 71 performs photoelectric conversion on an image formed on the light receiving surface as illustrated in FIG. 4, and supplies the resulting image to the image correction processing unit 81.

As illustrated in FIG. 4, the EMU 73 detects the 3-orthogonal-axis acceleration and angular velocity generated in the IMU 73 itself, and supplies them as sensor data to the processing circuit of the logic circuit board 72.

The image correction processing unit 81 performs necessary processing, such as defect correction, noise reduction, and aberration correction, on the image from the image sensor 71. When the measurement device 61 is used in, for example, an outdoor environment, automatic exposure control or automatic gain control may be performed to control the signal value of an image within a certain range so that the feature point detection and tracking processing unit 82 in the subsequent stage can appropriately perform feature point detection. In addition or instead, tone correction may be performed such as y correction.

The image correction processing unit 81 supplies the processed image to the feature point detection and tracking processing unit 82.

The feature point detection and tracking processing unit 82 performs image recognition processing on the image from the image correction processing unit 81. The image recognition processing detects the positions of feature points of a predetermined pattern on an image plane. A feature point may be an edge, a corner, or the like of an object. A two-dimensional coordinate system set on the image plane is referred to as an image coordinate system.

The feature point detection and tracking processing unit 82 performs tracking processing for tracking the detected positions of the feature points from within the image on the image of the frame in which the feature points have been detected. The feature point detection and tracking processing unit 82 supplies the detected positions of the feature points to the self-position estimation processing unit 84.

The IMU correction processing unit 83 corrects the sensor data of acceleration and angular velocity from the IMU 73 to reduce bias components (including drift components) and noise components, which are included in the sensor data. The correction processing in the IMU correction processing unit 83 is not limited to specific processing. The IMU 73 may include a geomagnetic sensor, and the IMU correction processing unit 83 may correct the sensor data of acceleration and angular velocity from the IMU 73 by using sensor data from the geomagnetic sensor.

The IMU correction processing unit 83 calculates the position, orientation, and velocity of the corresponding measurement device 61 based on the acceleration and angular velocity (corrected acceleration and angular velocity, hereinafter the same) from the IMU 73.

The IMU correction processing unit 83 supplies the acceleration and angular velocity from the IMU 73 and the position, orientation, and velocity calculated from the acceleration and angular velocity to the self-position estimation processing unit 84. In other words, the IMU correction processing unit 83 supplies the position, orientation, velocity, acceleration, and angular velocity of the corresponding measurement device 61 to the self-position estimation processing unit 84.

Based on the positions of the feature points from the feature point detection and tracking processing unit 82 and the position, orientation, velocity, acceleration, and angular velocity of the corresponding measurement device 61 from the IMU correction processing unit 83, the self-position estimation processing unit 84 estimates the position, orientation, and the like of the corresponding measurement device 61 in a world coordinate system. Self-position estimation processing for estimating the position and orientation of the measurement device 61 will be described later. The world coordinate system is a three-dimensional coordinate system set in a three-dimensional space in which the subject person who wears the measurement device 61 is located.

The self-position estimation processing unit 84 supplies data such as the estimated position and orientation of the corresponding measurement device 61 to the data transmission and reception unit 87.

The initialization processing unit 85 performs initialization processing based on data temporarily stored in the RAM 86 and the data from the self-position estimation processing unit 84. In the initialization processing, an initial position, initial orientation, and the like of the measurement device 61 in the world coordinate system are calculated. Details of the initialization processing will be described later. The initialization processing unit 85 supplies data such as the calculated initial position, initial orientation, and the like of the measurement device 61 to the self-position estimation processing unit 84.

The RAM 86 temporarily stores data necessary for the initialization processing in the initialization processing unit 85 and the like.

The data transmission and reception unit 87 controls communication with the communication device 63 of FIG. 4 to exchange various types of data with the information processing device 64 via the communication device 63. The data transmission and reception unit 87 supplies various types of data such as the position, orientation, and the like from the self-position estimation processing unit 84 to the information processing device 64 via the communication device 63 of FIG. 4.

<Processing of Initializing Measurement Devices 61>

Figure 6:
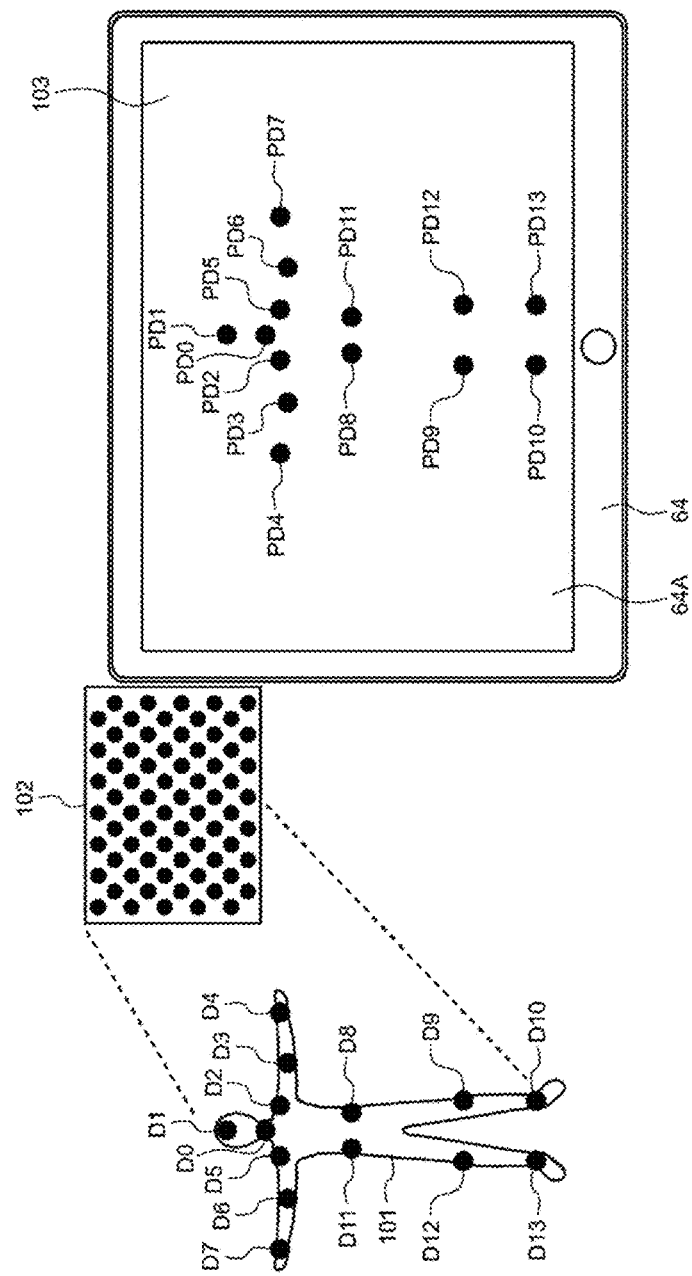
FIG. 6 is a diagram for explaining processing of initializing measurement devices.

FIG. 6 is a diagram for explaining processing of initializing measurement devices 61.

In FIG. 6, measurement devices D0 to D13, which correspond to measurement devices 61, are attached to parts of a subject person 101 whose motion is to be captured. The measurement devices D0 to D13 are attached to the neck, head, right shoulder, right elbow, right wrist, left shoulder, left elbow, left wrist, right waist, right knee, right ankle, left waist, left knee, and left ankle, respectively. Note that the parts and the number of measurement devices 61 to be attached to the subject person 101 are not, limited to those illustrated in FIG. 6.

At the time of performing the initialization processing, the measurement devices 61 (D0 to D13) attached to the parts of the subject person 101 capture an image of a chart 102 disposed at a predetermined position by their respective image sensors 71 (see FIGS. 4 and 5) to acquire the image of the chart 102.

The chart 102 has, for example, a pattern in which a large number of grid points arranged vertically and horizontally at regular intervals are drawn on the surface of a rectangular panel. The interval of the grid points is known.

The feature point detection and tracking processing unit 82 of each measurement device 61 detects the position of each grid point of the chart 102 in the image coordinate system (the position on the image plane) from the image acquired by the image sensor 71, and supplies the detected position to the initialization processing unit 85 via the self-position estimation processing unit 84.

Based on the position of each grid point of the chart 102 from the feature point detection and tracking processing unit 82, the initialization processing unit 85 calculates a relative orientation (including a relative position) of the corresponding measurement device 61 with respect to the chart 102 in the world coordinate system.

For example, a predetermined point on the surface of the chart 102 is set as the origin of the world coordinate system, two of the three orthogonal axes of the world coordinate system are set in the vertical and horizontal directions of the surface of the chart 102, and the other axis is set in the vertical direction perpendicular to the surface of the chart 102. However, the three orthogonal axes of the world coordinate system and the chart 102 only need to have a certain relationship. Thus, the initialization processing unit 85 can identify the position and orientation of the corresponding measurement device 61 in the world coordinate system based on the relative orientation in the world coordinate system between the chart 102 and the corresponding measurement device 61.

Based on the positions of the grid points of the chart 102, the interval of adjacent grid points, the gradient of grid points that connects grid points vertically and horizontally, and the like, which are from the feature point detection and tracking processing unit 82, the initialization processing unit 85 calculates and identifies the position and orientation (initial position and initial orientation) of the corresponding measurement device 61 in the world coordinate system at the time when the chart 102 was captured.

Data necessary for calculating the initial orientation and initial position are supplied from the information processing device 64 to each measurement device 61 and then stored in the RAM 86, to be referred to by the initialization processing unit 85.

The self-position estimation processing unit 84 of each measurement device 61 starts the self-position estimation processing when the initial position and the initial orientation are identified by the initialization processing. In the self-position estimation processing, the self-position estimation processing unit 84 estimates the position and orientation of the corresponding measurement device 61 based on the acceleration and angular velocity detected by the IMU 73 and based on the image acquired by the image sensor 71.

The measurement devices 61 do not need to be subjected to the initialization processing at the same time. For example, when the subject person 101 changes his/her own position, orientation, or posture, the chart 102 is switched between the measurement devices 61 within the capture range in this way, the measurement devices 61 may be subjected to the initialization processing step by step instead of at the same time.

When the self-position estimation processing unit 84 of the measurement device 61 that has been subjected to the initialization processing starts the self-position estimation processing, the position and orientation of the measurement device 61 estimated by the self-position estimation processing are transmitted to the information processing device 64.

The information processing device 64 determines whether or not the processing of initializing each measurement device 61 has been completed depending on either whether or not the information processing device 64 has received data such as the position and orientation from the measurement device 61 or whether or not the information processing device 64 has received a notification from the measurement device 61 indicating that the processing of initializing the measurement device 61 has been completed.

When the processing of initializing all the measurement devices 61 is completed, the information processing device 64 causes a display 64A of the information processing device 64 of FIG. 6 to display a device layout image 103. The device layout image 103 is a two-dimensional image that represents the positions (three-dimensional coordinates) in the world coordinate system supplied from the measurement devices 61. As a result, positions PD0 to PD13 of the measurement devices D0 to D13 worn by the subject person 101 are displayed as the device layout image 103 on the display 64A. The user refers to the device layout image 103 to set a connection relationship of the measurement devices D0 to D13 based on, for example, the human skeleton. Setting of the connection relationship of the measurement devices 61 will be described later.

<Procedure of Initialization Processing>

Figure 7:
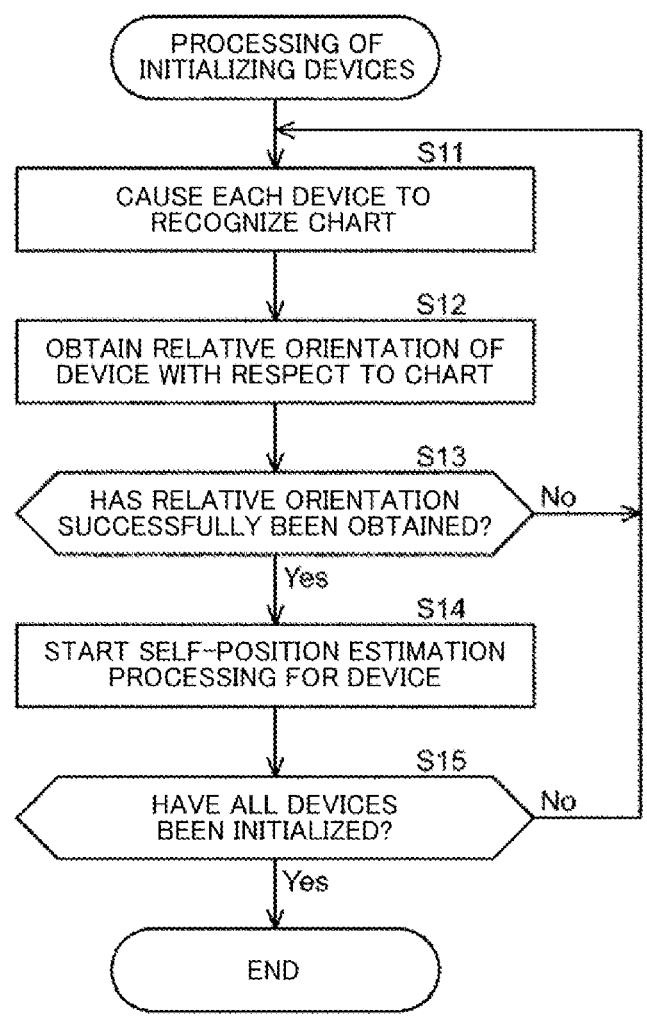
FIG. 7 is a flowchart illustrating an example of a procedure of the processing of initializing the measurement devices.

FIG. 7 is a flowchart illustrating an example of a procedure of the processing of initializing the measurement devices 61.

In FIG. 7, in step S11, the information processing device 64 (see FIG. 4) instructs each measurement device 61 to perform the initialization processing, and thus causes the image sensor 71 of the measurement device 61 to capture an image of the chart 102 so that, the feature point detection and tracking processing unit 82 recognizes the chart 102. The processing proceeds from step S11 to step S12.

In step S12, the initialization processing unit 85 of each measurement device 61 obtains a relative orientation of the measurement device 61 with respect to the chart 102 in the world coordinate system based on the chart 102 recognized in step S11. The processing proceeds from step S12 to step S13.

In step S13, the initialization processing unit 85 of each measurement device 61 determines whether or not the relative orientation has successfully been obtained in step S12.

If it is determined in step S13 that the relative orientation has not successfully been obtained, the processing is returned from step S13 to step S11, and is repeated from step S11.

If it is determined in step S13 that the relative orientation has successfully been obtained, the processing proceeds to step S14, and then the self-position estimation processing unit 84 starts the self-position estimation processing. The processing proceeds from step S14 to step S15.

In step S15, the information processing device 64 determines whether all the measurement devices 61 have been initialized.

If it is determined in step S15 that not all measurement devices 61 have been initialized, the processing is returned from step S15 to step S11, and is repeated from step S11 for the measurement devices that are yet to be initialized.

If it is determined in step S15 that all the measurement devices 61 have been initialized, the processing of initializing the devices ends.

<Other Methods for Initializing Measurement Devices 61>

The processing of initializing the measurement devices 61 described above is an example, and it is not limited to the above-described method.

As another method for processing of initializing the measurement devices 61, a first method or a second method described below may be used.

(First Method for Another Initialization Processing)

In the first method for another processing of initializing the measurement devices 61, a distance measurement device such as a time-of-flight (ToF) camera or a stereo camera is used to acquire an image of the chart 102 in advance. The position of the distance measurement device when the image was captured is also acquired. The position of the distance measurement device is a position in the world coordinate system set with reference to the chart 102 as in the above-described method for initialization. The image of the chart 102 acquired by the distance measurement device is supplied as a key frame from the information processing device 64 to each measurement device 61 and stored in the RAM 85. Similarly, the position of the distance measurement device when the key frame was acquired is stored in the RAM 85.

The initialization processing unit 85 of each measurement device 61 compares the image from the image sensor 71 with the key frame image stored in the RAM 85 to obtain the degree of similarity between the images. As a result, when the degree of similarity reaches or exceeds a predetermined threshold value, the initialization processing unit 85 obtains a relative orientation of the image plane of the image from the image sensor 71 with respect to the image plane (perspective projection plane) of the key frame image in the world coordinate system (for example, A. Kasyanov, F. Engelmann, J. Stuckler, and B. Leibe. "Keyframe-Based Visual-Inertial Online SLAM with Relocalization," InIROS, 2017). The initialization processing unit 85 then identifies the initial orientation and initial position of the measurement device 61 in the world coordinate system based on the obtained relative orientation and the position of the distance measurement device stored in the RAM 85.

The comparison (matching) between the image from the image sensor 71 and the key frame image may be performed not on the entire image but on feature points in the image. In this comparison, extracted features are transformed to feature descriptions, such as Scale-Invariant Feature Transform (SIFT) or Speeded Up Robust Features (SURF), to evaluate the features by matching them, (Second Method for Another Initialization Processing)

In the second method for another processing of initializing the measurement devices 61 the initialization processing unit 85 acquires a pair of parallax images (movement parallax images) captured by an image sensor 71 at, two different positions when the position of a measurement devices 61 change. The initialization processing unit 85 detects the positions of image feature points, in the acquired pair of parallax images, corresponding to predetermined feature points of a subject (physical).

Then, the initialization processing unit 85 uses the positions of the image feature points detected in the pair of parallax images and the amount of movement of the camera (image sensor 71) to obtain three-dimensional coordinates of the feature points on the physical subject corresponding to the image feature points in the camera coordinate system with the origin being the camera in the manner of triangulation.

Figure 8:
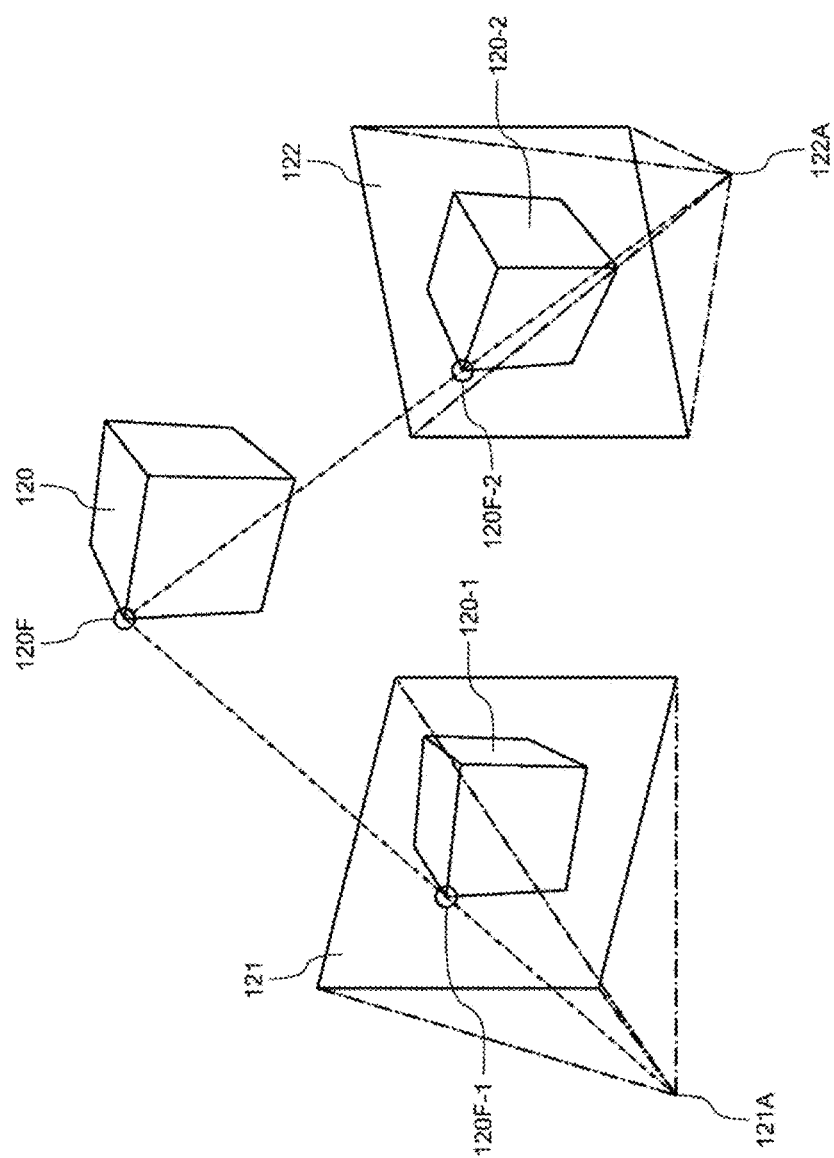
FIG. 8 is a diagram illustrating an example of a correspondence relationship between a predetermined feature point of a subject and feature points on a pair of parallax images.

FIG. 8 is a diagram illustrating an example of a correspondence relationship between a predetermined feature point of a subject and feature points on a pair of parallax images.

A subject 120 in FIG. 8 is, for example, a cuboid object captured by the image sensor 71, and image planes (perspective projection planes) 121 and 122 represent virtual image planes on which a pair of parallax images captured by the image sensor 71 at different positions is projected.

Viewpoints (principal points) 121A and 122A represent the focal positions of lenses when the subject projected onto the image planes 121 and 122 was captured, respectively.

It is assumed that images 120-1 and 120-2 of the subject 120 captured from the viewpoints 121A and 122A appear on the image planes 121 and 122, respectively.

It is also assumed that vertices of the subject 120 are set as feature points, and image feature points corresponding to the feature points of the subject 120 are detected.

In this case, when the image sensor 71 is at the position of the viewpoint 121A, an image feature point 120F-1 is detected at a position where a line segment connecting a feature point 120F of the subject 120 and the viewpoint 121A intersects the image plane 121.

Further, when the image sensor 71 is at the position of the viewpoint 122A, an image feature point 120F-2 is detected at a position where a line segment connecting the feature point 120F of the subject 120 and the viewpoint 122A intersects the image plane 122. The other vertices of the subject 120 are similarly detected as image feature points in the pair of parallax images.

Assuming that the amount of parallax (the distance between the viewpoints 121A and 122A) is known, the three-dimensional coordinates of the subject in the camera coordinate system can be determined based on the positions of the image feature points detected in each of the image planes 121 and 122, or using the principle of triangulation or the like. By redefining this camera coordinate system as a world coordinate system and registering the three-dimensional coordinates and camera image of this subject as a key frame, the position and orientation of the camera in the common world coordinate system can be obtained when the same subject is captured by another measurement device 61. Accordingly, the position and orientation of the measurement device 61 in the world coordinate system can be identified. A three-dimensional structure (including the positions of the vertices, etc.) of the subject 120 in the world coordinate system can also be calculated.

On the other hand, the amount of parallax can be detected using an existing method of monocular visual-inertial SLAM initialization processing. Specifically, the position of the measurement device 61 is estimated by integrating the IMU 73 (inertial measurement) of the measurement device 61 and visual simultaneous localization and mapping (SLAM) using the image sensor 71. As a result, the bias included in the sensor data from the IMU 73 is corrected, and a moving distance is detected from the image with high accuracy, so that the amount of parallax can be detected with high accuracy (for example, Tong Qin, Peiliang Li, and Shaojie Shen, "VINS-Mono: A Robust and Versatile Monocular Visual-Inertial State Estimator," arXiv 2017, arXiv: 1708.03852).

When the processing of initializing the measurement devices 61 is performed, the feature point detection and tracking processing unit 82 detects the positions of feature points of a predetermined pattern in the image from the image sensor 71 and supplies the positions to the initialization processing unit 85.

When the positions of the feature points supplied from the feature point detection and tracking processing unit 82 are changed, the initialization processing unit 85 acquires the positions of the image feature points before and after the change in the pair of parallax images.

Based on the sensor data from the IMU 73 and the image from the image sensor 71, the initialization processing unit 85 (or the self-position estimation processing unit 84) estimates the position of the measurement device 61 by integrating the IMU 73 (inertial measurement) and visual SLAM. As a result, the initialization processing unit 85 detects the amount of parallax, and identifies the initial position and initial orientation of the measurement device 61 in the world coordinate system by the above-described processing.

In the measurement device 61 that has been subjected to the initialization processing in this way, the image used in the initialization processing may be used as a key frame, and the key frame and the three-dimensional structure of the subject may be supplied to another measurement device 61. As a result, the other measurement device 61 obtains a relative orientation of the image plane of the image from the image sensor 71 with respect to the image plane of the key frame image based on the three-dimensional structure of the subject, so that the initial position and initial orientation of the measurement device 61 can be identified.

<Self-Position Estimation Processing>

Next, processing after the processing of initializing the measurement devices 61 will be described.

After the processing of initializing the measurement devices 61 is completed, the image from the image sensor 71 is supplied to the image correction processing unit 81, and the acceleration and angular velocity output from the IMU 73 are supplied to the IMU correction processing unit 83. (Processing in Image Correction Processing Unit 81 and Feature Point Detection and Tracking Processing Unit 82)

The image supplied to the image correction processing unit 81 is subjected to predetermined correction processing and then supplied to the feature point detection and tracking processing unit 82.

The feature point detection and tracking processing unit 82 detects feature points and tracks the feature points in the image from the image correction processing unit 81.

The feature points may be a pattern suitable for image matching in subsequent steps (pattern to facilitate identification).

Any method such as the Harris algorithm can be used as a method of detecting the feature points.

When detecting feature points in the image of a predetermined frame from the image correction processing unit 81, the feature point detection and tracking processing unit 82 tracks the feature points in the subsequent frame images to determine the positions of the detected feature points appearing in the images.

Any method such as a zero-mean normalized crosscorrelation (ZNCC) method or a Kanade-Lucas-Tomasi (KLT) method can be used as a method of tracking the feature points.

In tracking of the feature points by the ZNCC method or the KLT method, a small image of, for example, 8×8 pixels including the image of a feature point is set as the small image to be tracked. Then, a small area most similar to the small image to be tracked is detected from among predetermined search areas in the frame image in which the feature point is to be tracked.

The search areas may be limited to areas according to results of predicting the motion of the measurement device 61 using the sensor data from the IMU 73.

Figure 9:
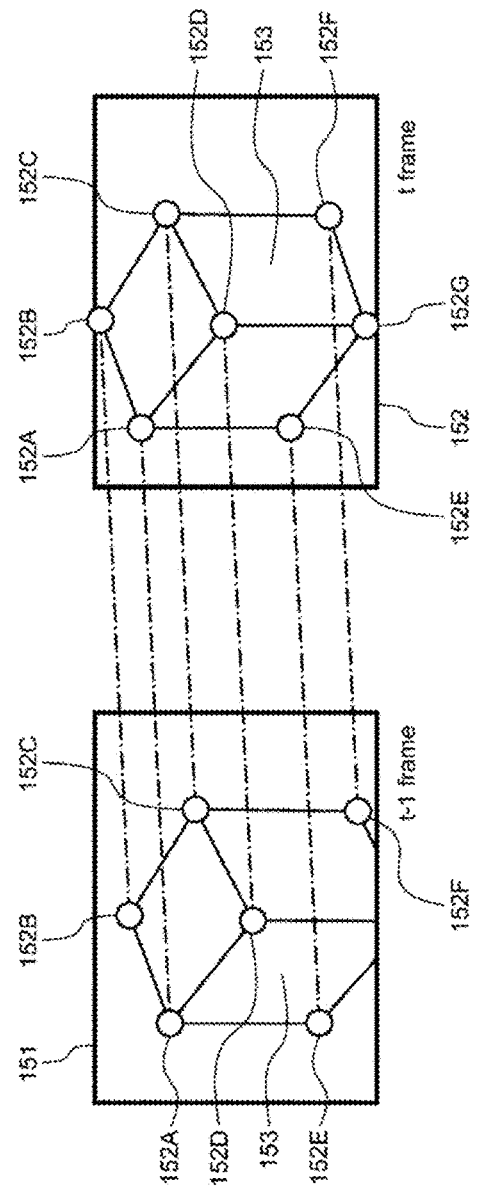
FIG. 9 is a diagram illustrating an example of how feature points are tracked.

FIG. 9 is a diagram illustrating an example of how feature points are tracked.

In FIG. 9, images 151 and 152 are images from the image sensor 71 supplied to the feature point detection and tracking processing unit 82. The image 152 is a frame image supplied after a predetermined time step with respect to the image 151.

In the image 151, vertices of a subject 153 are detected as feature points 152A to 152F.

In the image 152, the position or the like of the subject 153 in the image 152 has changed due to a change in the position or orientation of the measurement device 61 as compared to the image 151 when captured.

By tracking the feature points on the image 152 in the feature point detection and tracking processing unit 82, the positions of the feature points 152A to 152F in the image 152 corresponding to the feature points 152A to 152E in the image 151 are detected. A feature point 152G in the image 152 that has not been detected in the image 151 is newly detected.

The positions of the image feature points detected by the feature point detection and tracking processing unit 82 are supplied as two-dimensional coordinates on the image plane (in the image coordinate system) from the feature point detection and tracking processing unit 82 to the self-position estimation processing unit 84.

In a case where the positions of the feature points on the physical subject corresponding to the image feature points can be detected as the positions (three-dimensional coordinates) in the world coordinate system, not only the positions (two-dimensional coordinates) of the image feature points but also the positions (three-dimensional coordinates) of the feature points on the physical subject may be supplied from the feature point detection and tracking processing unit 82 to the self-position estimation processing unit 84.

(Processing in IMU Correction Processing Unit 83)

The IMU correction processing unit 83 integrates the acceleration and angular velocity supplied from the IMU 73 in time series to calculate the position, orientation, and velocity of the corresponding measurement device 61 according to inertial navigation.

In calculating the position and orientation of the corresponding measurement device 61, the initial position and initial orientation of the measurement device 61 (IMU 73) are obtained from the initialization processing unit 85.

The sensor data from the IMU 73 includes a measurement error called a bias. The bias is an offset, and as it is integrated, the error is gradually enhanced. In order to suppress this enhanced error, it is necessary to estimate and correct the bias value. In addition, the IMU 73 alone cannot detect the translational velocity and cannot distinguish whether the subject is stationary or is translationally moving at a constant velocity, so that it is necessary to estimate the initial velocity. As such necessary information, an estimated value estimated by the self-position estimation processing unit 84 described later can be used.

An acceleration and an angular velocity, which are observation values observed by the IMU 73 at a time t, are expressed by the following Equations (1) and (2). Variables $a_t$ and $\omega_t$ with a caret on the left side represent an acceleration and an angular velocity (both vectors) observed by the IMU 73, respectively.

[Math. 1]

$$\hat{a}_t = a_t + b_a + R_w^{I_t} g^w + n_a \quad (1)$$

where $a_t$ is a true acceleration, $b_a$ is an acceleration bias, $R_w^{I_t}$ is a transformation from world coordinates to local coordinates, $R_w^{I_t} g^w$ is the acceleration of gravity in local coordinate system, and na is an acceleration noise.

[Math. 2]

$$\hat{\omega}_t = \omega_t + b_\omega + n_\omega \quad (2)$$

where $\omega_t$ is a true angular velocity, $b_\omega$ is an angular velocity bias, and $n_\omega$ is an angular velocity noise.

According to inertial navigation using the observed values from the IMU 73, the position, velocity, and orientation of the measurement device 61 are calculated by the following Equations (3) to (5), respectively.

[Math. 3]

$$p_{b_{k+1}}^w = p_{b_k}^w + v_{b_k}^w \Delta t_k + \int\int_{t \in [t_k, t_{k+1}]} \left( R_{I_t}^w (\hat{a}_t - b_{a_t} - n_a) - g^w \right) dt^2 \quad (3)$$

[Math. 4]

$$v_{b_{k+1}}^w = v_{b_k}^w + \int_{t \in [t_k, t_{k+1}]} \left( R_{I_t}^w (\hat{a}_t - b_{a_t} - n_a) - g^w \right) dt \quad (4)$$

[Math. 5]

$$q_{b_{k+1}}^w = q_{b_k}^w \otimes \int_{t \in [t_k, t_{k+1}]} \frac{1}{2} \Omega(\hat{\omega}_t - b_{\omega_t} - n_\omega) q_t^{b_k} dt \quad (5)$$

where $q_{b_k}^w$ is a quaternion, and $\otimes$ is a quaternion product operator.

Here, $\Omega(\omega)$ is represented by the following Equations (6) and (7).

[Math. 6]

$$\Omega(\omega) = \begin{bmatrix} [\omega]_\times & \omega \\ -\omega^T & 0 \end{bmatrix} \quad (6)$$

[Math. 7]

$$[\omega]_\times = \begin{bmatrix} 0 & -\omega_z & \omega_y \\ \omega_z & 0 & -\omega_x \\ -\omega_y & \omega_x & 0 \end{bmatrix} \quad (7)$$

In Equations (3) to (5), k represents a frame number given to the image frame acquired from the image sensor 71 in chronological order. In a case where the sensor data acquired from the IMU 73 is indicated by a data number in chronological order, $b_k$ represents the data number when an image with frame number k was acquired.

The acceleration bias and angular velocity bias (hereinafter also referred to as the biases of the IMU 73) included in the sensor data from the IMU 73 and the initial velocity of the measurement device are estimated by the self-position estimation processing unit 84 and supplied to the IMU correction processing unit 83.

The position, velocity, and orientation of the corresponding measurement device 61 calculated by Equations (3) to (5) are supplied to the self-position estimation processing unit 84. The position and velocity are three-dimensional vectors, and the orientation is a quaternion (four-dimensional vector).

(Processing in Self-Position Estimation Processing Unit 84)

The self-position estimation processing unit 84 estimates the biases of the IMU 73 and the initial velocity of the measurement device 61 by optimization processing to be iterated or filtering processing based on a Kalman filter.

In either processing, the biases of the IMU 73 and the initial velocity of the measurement device are estimated and also the position and orientation of the measurement device 61 are corrected so that the error in a reprojected image is reduced, so that a difference is reduced between the position and orientation of the measurement device 61 estimated using only the IMU 73 and the position and orientation of the measurement device 61 estimated through the processing in the self-position estimation processing unit 84, and so that the variation in the biases of the IMU 73 is minimized.

The processing of correcting the position and orientation of the measurement device 61 is referred to as self-position estimation processing.

As methods of self-position estimation processing, specifically, there are known a method in which the IMU 73 (inertial measurement) of the measurement device 61 and visual simultaneous localization and mapping (SLAM) using the image sensor 71 are integrated (for example, Qin, T., Li, P.; Shen, S., "VINS-Mono: A Robust and Versatile Monocular Visual-Inertial State Estimator," arXiv 2017, arXiv:1708.03852) and a method based on the following Kalman filter (for example, P. Geneva, K. Eckenhoff, W. Lee, Y. Yang, and G. Huang, "OpenVINS: A Research Platform for Visual-Inertial Estimation," IROS Workshop on Visual-Inertial Navigation: Challenges and Applications, 2019).

In the present embodiment, only the outline of a case based on the latter method (multi-state constraint Kalman filter (MSCKF) method) with less processing load will be described.

In the self-position estimation processing unit 84, a state to be estimated (state variable) is represented by $x_k$. The state variable $x_k$ is represented by the following Equation (8).

[Math. 8]

$$x_k = [x_I^T, x_C^T, x_W^T] \quad (8)$$

Here, $x_I$, $x_C$, and $x_W$ are represented by the following Equations (9) to (11).

[Math. 9]

$$x_I = [(\bar{q}_{I_k}^W)^T, (p_{I_k}^W)^T, (v_{I_k}^W)^T, (b_{\omega_k})^T, (b_{a_k})^T] \quad (9)$$

[Math. 10]

$$x_C = [(\bar{q}_{I_{k-1}}^W)^T, (p_{I_{k-1}}^W)^T, \ldots (\bar{q}_{I_{k-c}}^W)^T, (p_{I_{k-c}}^W)^T] \quad (10)$$

[Math. 11]

$$x_w = [(\bar{q}_I^C)^T, (\bar{p}_I^C)^T] \quad (11)$$

Here, the state variable $x_I$ represents an orientation q, a position p, a velocity v, an angular velocity bias $b\omega$, and an acceleration bias $b_a$ of the IMU 73. The orientation q is a quaternion, and the position p, velocity v, angular velocity bias $b_\omega$, and acceleration bias $b_a$ are each a three-dimensional vector.

The state variable $x_C$ represents the history of the past orientation q and position p of the corresponding measurement device 61.

Besides, k represents a time step (number) at which the image of a k-th frame is acquired from the image sensor 71.

An error covariance of the system based on the Kalman filter (analysis error covariance) is represented by the following Equation (12).

[Math. 12]

$$P_{k|k-1} = \Phi_{k-1} P_{k-1|k-1} \Phi_{k-1}^T + Q_{k-1} \quad (12)$$

where $\Phi_{k-1}$ is a propagation matrix for the system, and $Q_{k-1}$ is a covariance of system noise.

The subscript k|k−1 indicates a predicted value of the state variable at time step k predicted from the value at time step k−1.

The Kalman gain K is represented by the following Equation (13).

[Math. 13]

$$K_k = P_{k|k-1} H_k^T (H_k P_{k|k-1} H_k^T + R_{m,k})^{-1} \quad (13)$$

Meanwhile, an estimated value of the state variable is calculated by the following Equation (14).

[Math. 14]

$$\hat{x}_{k|k} = \hat{x}_{k|k-1} \boxplus K_k(z_{m,k} - h)(\hat{x}_{k|k-1})) \quad (14)$$

The first term on the right side is a predicted value of the state variable at time step k calculated based on a propagation formula for the IMU 73 using a propagation matrix $\Phi k-1$ for the system, and also represents a predicted value of the state variable at time step k predicted from the value at time step k−1.

Besides, Zm,k represents the position of an image feature point detected from the image at time step k (position in the image coordinate system). Also, Zm,k is an observed value given from the feature point detection and tracking processing unit 82 to the self-position estimation processing unit 84.

It is assumed that the positions of the feature points, in the world coordinate system, on the subject (feature points on the physical subject) corresponding to the detected image feature points are determined. It is also assumed that the predicted value of the state variable at time step k is applied as the current (time step k) position and orientation of the measurement device 61. In this case, the position of the image feature point corresponding to a feature point on the physical subject is estimated based on the predicted value of the position and orientation of the measurement device 61 at time k.

In Equation (14), the estimated position (two-dimensional coordinates) of the image feature point is the value of h(x) (as simply expressed) in parentheses in the second term on the right side. Then, in Equation. (14), a reprojection error, which is a difference between the value of h(x) and Zm,k, is obtained, and the state variable is updated with the reprojection error weighted with the Kalman gain K. As a result, an estimated value of the state variable is calculated such that the reprojection error is closer to zero.

The Kalman gain K at time step k in Equation (13) is calculated based on an error covariance P of the system at time step k predicted from the value at time step k−1 (analysis error covariance P) and based on an error covariance R observed at time step k (observation error covariance R). Specifically, the Kalman gain K at time step k is updated such that, of the predicted value of the state variable at time step k predicted from the value at time step k−1 and the observed value observed at time k, the one with higher reliability is given a higher weight (such that the smaller the error covariance, the higher the weight).

The error covariance P of the system at time step k is updated by the following Equation (15).

[Math. 15]

$$P_{k|k} = P_{k|k-1} - K_k H_k P_{k|k-1} \quad (15)$$

According to the multi-state constraint Kalman filter (MSCKF) method, not only the current state variable value of the measurement device 61 (IMU 73) but also the past state variable values are simultaneously updated by the Kalman filter. As a result, the value of the state variable such as the position and orientation of the measurement device 61 is estimated with high accuracy such that it is consistent with the past values.

The self-position estimation processing unit 84 transmits the estimated value of the state variable estimated as described above from the data transmission and reception unit 87 (see FIG. 5) to the information processing device 64 via the communication device 63 (see FIG. 4).

Specifically, the self-position estimation processing unit 84 transmits the estimated value of the current (latest) position and orientation of the corresponding measurement device 61 as position and orientation data to the information processing device 64.

The self-position estimation processing unit 84 transmits to the information processing device 64 the feature point data related to two-dimensional coordinates and three-dimensional coordinates of the feature points in each frame, which are tracked over multiple frames from the feature point detection and tracking processing unit 82 used to estimate the state variable, and the error covariance data related to the error covariance P of the system calculated by Equation (15).

The self-position estimation processing unit 84 provides the estimated values of the acceleration bias and angular velocity bias of the IMU 7 (biases of the IMU 73); and the velocity of the measurement device 61, which are included in the estimated state variable, to the IMU correction processing unit 83. The IMU correction processing unit 83 uses the estimated values supplied from the self-position estimation processing unit 84 to calculate the position, velocity, and orientation of the corresponding measurement device 61 by using Equations (3) to (5).

<Functional Configuration of Information Processing Device 64>

Figure 10:
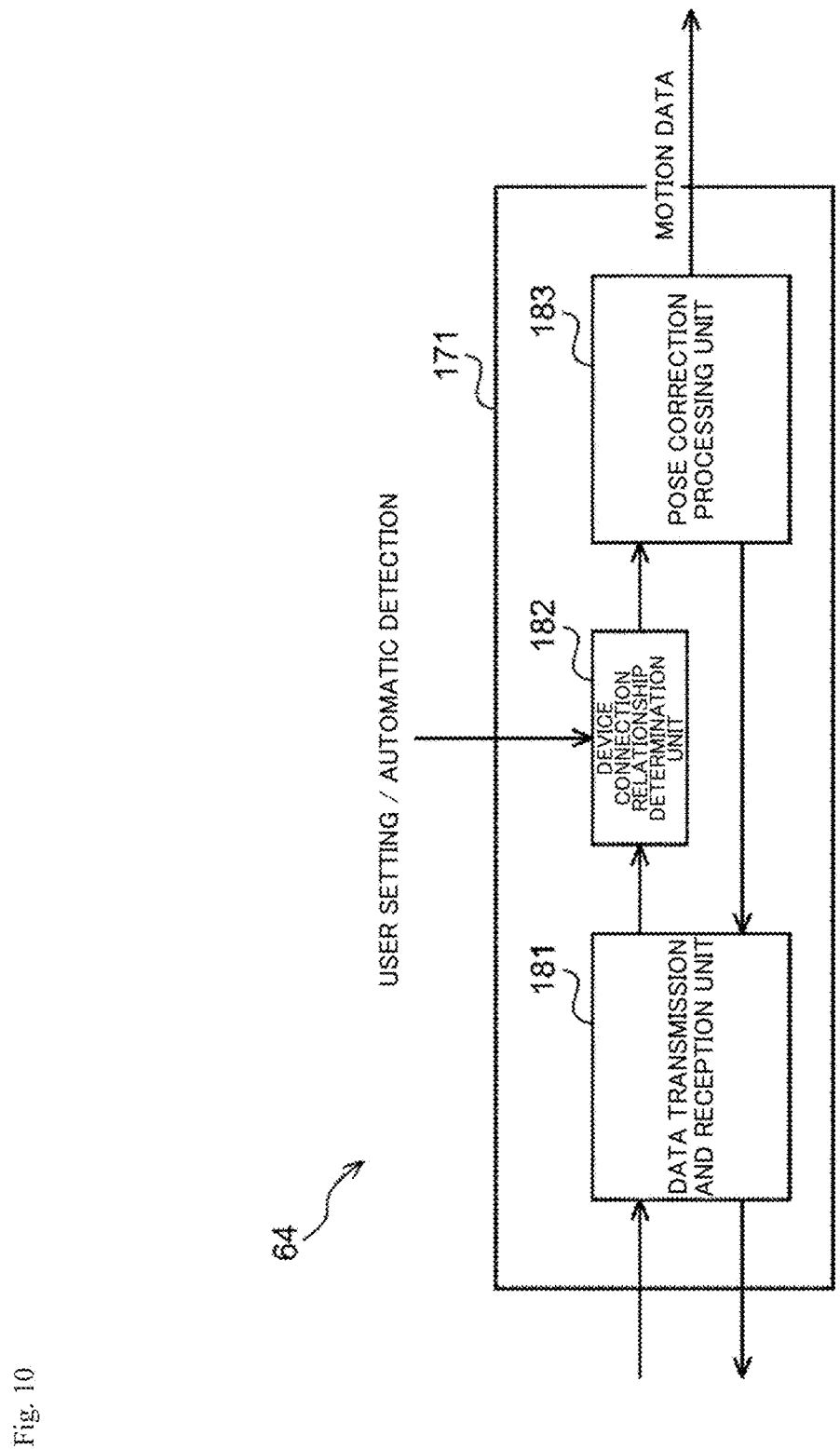
FIG. 10 is a block diagram illustrating an example of a functional configuration of the information processing device of FIG. 4.

FIG. 10 is a block diagram illustrating an example of a functional configuration of the information processing device 64 of FIG. 4.

In FIG. 10, the information processing device 64 includes a posture estimation unit 171. The posture estimation unit 171 acquires the position and posture data, feature point data, and error covariance data from each of the measurement devices 61 attached to the parts of the subject person 101.

The posture estimation unit 171 sets a connection relationship of the measurement devices 61.

Then, the posture estimation unit 171 corrects (updates) the position and orientation (estimated value) supplied from each measurement devices 61 based on the data supplied from each measurement device 61 and the connection relationship of the measurement devices 61, and outputs to another processing unit the resulting positions and orientations as pose data that represents the overall posture of the subject person. The pose data output from the posture estimation unit 171 may be used for any processing, and is not limited to being used for specific processing.

The posture estimation unit 171 corrects the position and orientation from each measurement device 61 in consideration of the connection relationship of the measurement devices 61, so that the posture (or motion) of the subject person can be detected with high accuracy.

The posture estimation unit 171 includes a data transmission and reception unit 181, a device connection relationship determination unit 182, and a pose correction processing unit 183.

The data transmission and reception unit 181 controls communication with the communication device 63 of FIG. 4 to exchange various types of data with each measurement device 61 via the communication device 63. The data transmission and reception unit 181 acquires the position and orientation data, feature point data, and error covariance data, which have been transmitted from the self-position estimation processing unit 84 of each measurement device 61.

The data transmission and reception unit 181 supplies the data acquired from each measurement device 61 to the device connection relationship determination unit 182 and the pose correction processing unit 183.

The device connection relationship determination unit 182 (connection relationship setting unit) sets a connection relationship of the measurement devices 61 based on the position and orientation (estimated value) of each measurement device 61, which is the position and orientation data from each measurement device 61. The device connection relationship determination unit 182 supplies the set connection relationship to the pose correction processing unit 183.

The pose correction processing unit 183 corrects (updates) the position and orientation of each measurement device 61 based on the data from each measurement device 61 and the connection relationship of the measurement devices 61 from the device connection relationship determination unit 182. The pose correction processing unit 183 outputs to another processing unit or the like the corrected positions and orientations of the measurement devices 61 as pose data that represents the overall posture of the subject person 101. The pose correction processing unit 183 transmits to each measurement device 61 via the data transmission and reception unit 181 the corresponding corrected position and orientation.

In the self-position estimation processing unit 84 of each measurement device 61, the estimated value estimated as the position and orientation of the measurement device 61 are changed to the corrected position and orientation supplied from the pose correction processing unit 183. As a result, a predicted value of the state variable at the next time step is calculated using the corrected position and orientation values supplied from the pose correction processing unit 183.

(Processing in Device Connection Relationship Determination Unit 182)

The device connection relationship determination unit 182 performs processing of setting a connection relationship of the measurement devices 61 as initial setting.

For example, when the initialization processing is completed for all the measurement devices 61 in the processing of initializing the measurement devices 61 and then the self-position estimation processing is started, the device connection relationship determination unit 182 causes the display 64A of the information processing device 64 illustrated in FIG. 6 to display the device layout image 103 based on the positions of the measurement devices 61 supplied from the measurement devices 61.

The device layout image 103 of FIG. 6 represents a case where the measurement devices D0 to D13 as the measurement devices 61 are attached to the parts of the subject person 101. In this case, the positions PD0 to PD13 of the measurement devices D0 to D13 in the world coordinate system are displayed two-dimensionally in the device layout image 103.

The user refers to the device layout image 103 to set a connection relationship of the measurement devices D0 to D13 based on, for example, the skeletons.

Among combinations of any two measurement devices 61 out of the measurement devices D0 to D13, a combination in which no other measurement device is attached to a part along the skeleton between two measurement devices 61 is referred to as two measurement devices 61 having an adjacency relationship or two adjacent measurement devices 61. Further, among the combinations of two measurement devices 61 having such an adjacency relationship, a combination in which the distance between two measurement devices 61 is substantially constant even if the posture of the subject person 101 changes (a change in the distance is equal to or less than a predetermined threshold value) is referred to as two measurement devices 61 having a narrowly defined adjacency relationship.

The user sets a measurement device 61 (D0) at any position (for example, the position PD0) as a start point, and selects measurement devices 61 (D1, D2, and D5) having an adjacency relationship with the measurement device 61 (D0) by, for example, clicking their positions (positions PD1, PD2, and PD5) on the screen of the device layout image 103. Then, the user selects measurement devices 61 having an adjacency relationship (no for D1, D3 for D2, and D6 for D5) with each of the measurement devices 61 (D1, D2, and D5) selected as having an adjacency relationship with the measurement device 61 (DO) as the start point. The user repeats such selection to set a connection relationship of all the measurement devices 61 (D0 to D13) worn by the subject person 101.

The user may select only a combination of two measurement devices 61 having a narrowly defined adjacency relationship. Normally, two measurement devices 61 having an adjacency relationship are expected to be attached to the subject person 101 so that they have a narrowly defined adjacency relationship. Accordingly, in the following description, it is assumed that the two measurement devices 61 having an adjacency relationship have a narrowly defined adjacency relationship.

The setting of a connection relationship of the measurement devices 61 may be automatically performed by the information processing device 64 instead of being based on a user's selection. For example, if the skeleton of the subject person 101 is regarded as a general human skeleton, it is possible to estimate which part of the subject person 101 each measurement device 61 is attached to and automatically set a connection relationship of the measurement devices 61. Only two measurement devices 61 having a narrowly defined adjacency relationship may be automatically set as having an adjacency relationship.

When the connection relationship of the measurement devices 61 is set based on a user's selection and the like, the device connection relationship determination unit 182 of FIG. 10 connects the positions of the measurement devices 61 having an adjacency relationship with a straight line (referred to as a connection line).

Figure 11:
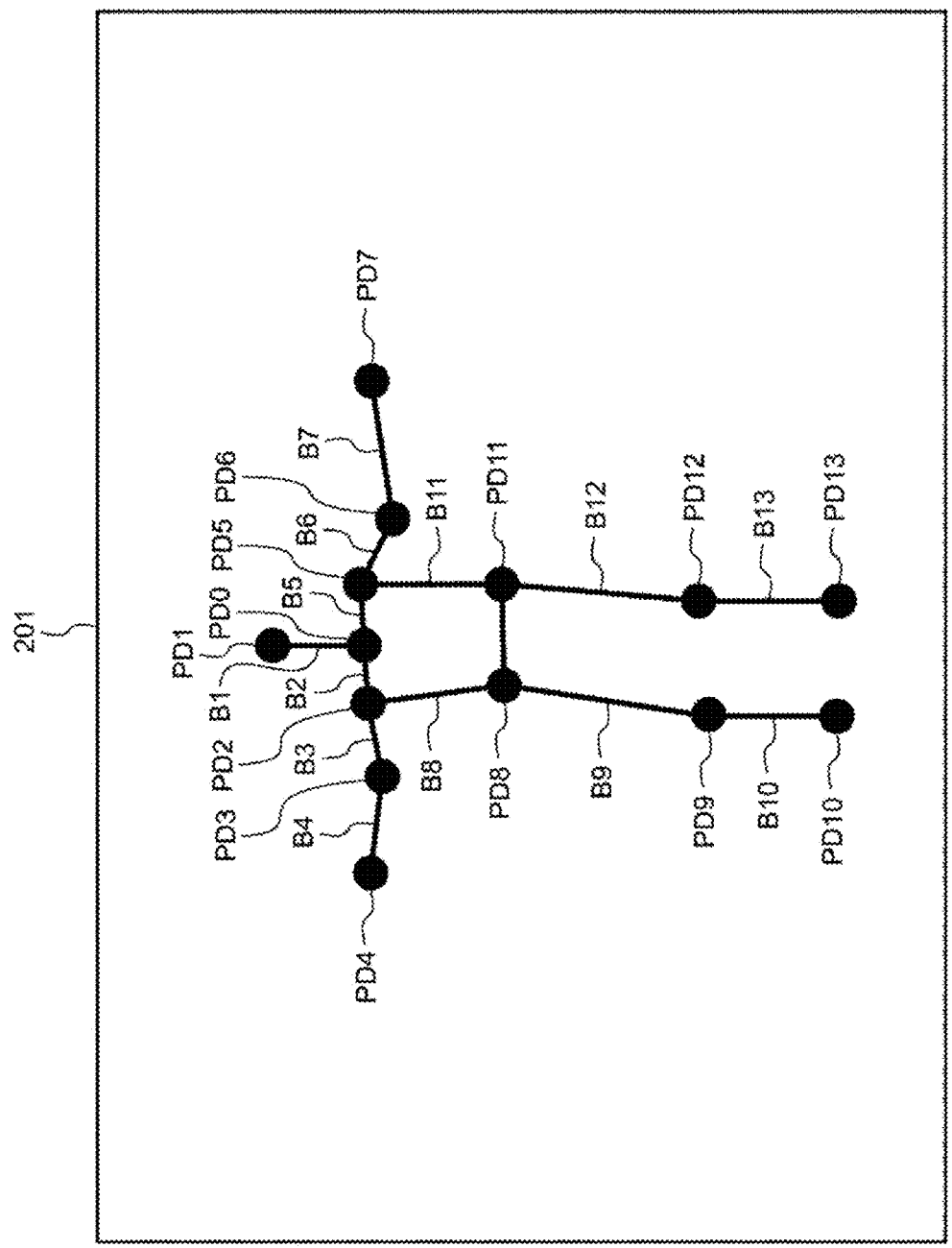
FIG. 11 is a diagram illustrating an example of a connection relationship image representing a connection relationship of measurement devices.

FIG. 11 is a diagram illustrating an example of a connection relationship image representing a connection relationship of the measurement devices 61.

The connection relationship image 201 in FIG. 11 corresponds to an example of attaching the measurement device 61 of FIG. 6, and the positions PD0 to PD13 of the measurement devices D0 to D13 illustrated in FIG. 6 appear in the connection relationship image 201.

On the other hand, the positions of the measurement devices 61 having an adjacency relationship are connected by straight connection lines B1 to B13 based on the connection relationship set by a user's selection or the like. These connection lines B1 to B13 represent the skeleton of the subject person 101. The device connection relationship determination unit 182 displays the connection relationship image 201 on the display of the information processing device 64 to allow the user to confirm whether the connection relationship is correctly set and to present which part of the subject person 101 each of the measurement devices D0 to D13 is attached to.

(Processing Procedure for Setting Device Connection Relationship)

Figure 12:
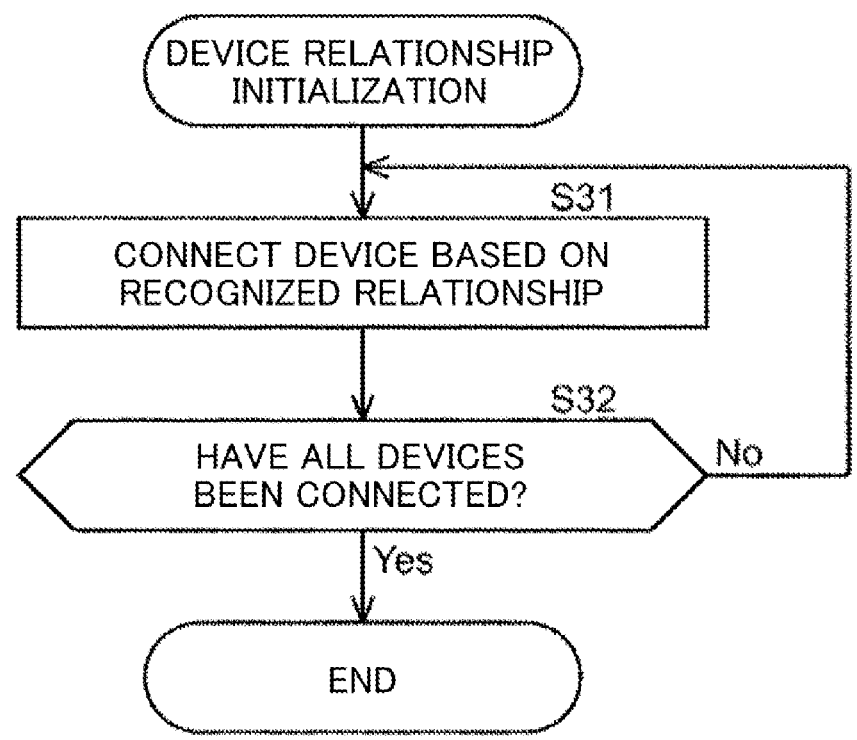
FIG. 12 is a flowchart illustrating an example of a procedure for setting the connection relationship of the measurement devices.

FIG. 12 is a flowchart illustrating an example of a procedure for setting the connection relationship of the measurement devices 61.

In FIG. 12, in step S31, the device connection relationship determination unit 182 recognizes the presence of each measurement device 61 by receiving position and orientation data from the measurement device 61, for example. Then, the device connection relationship determination unit 182 connects the measurement devices 61 by connection lines based on the adjacency relationship of the measurement devices 61 selected by the user. The processing proceeds from step S31 to step S32.

In step S32, the device connection relationship determination unit 182 determines whether or not all the measurement devices 61 have been connected to any other measurement device 61.

If it is determined in step S32 that not all the measurement devices 61 have been connected to any other measurement device 61, the processing is returned to step S31 to repeat steps S31 and S32.

If it is determined in step S32 that all the measurement devices 61 have been connected to any other measurement device 61, the processing of this flowchart ends.

(Processing in Pose Correction Processing Unit 183)

Based on the data from each measurement device 61, the pose correction processing unit 183 first sets, of all the measurement devices 61, measurement devices 61 for which the estimated values of the positions and orientations (hereinafter simply referred to as positions and orientations) supplied from the measurement devices 61 are to be corrected (updated).

Specifically, a measurement device 61 for which the error covariance of the system supplied from the measurement device 61 is equal to or greater than a predetermined threshold value, or a measurement device 61 in which the number of feature points supplied from the measurement device 61 is equal to or less than a predetermined threshold value, is set as an unreliable measurement device 61 to be updated.

In addition, if the distance between two measurement devices 61 having an adjacency relationship is equal to or greater than a predetermined threshold value, the measurement device 61 with the higher error covariance of the two measurement devices 61 is set to be updated. The threshold value for that distance may be a value obtained by adding a predetermined distance to a past distance, used as a reference, between two measurement devices 61 having an adjacency relationship.

If the position and orientation are represented by one multidimensional vector (referred to as a position and orientation vector), the distance between two measurement devices 61 corresponds to the norm of the difference between the position and orientation vectors supplied from the two measurement devices 61 (size of difference in position and orientation). The term "distance" or "norm" as used herein may be a distance involving only the position, a norm involving only the orientation, or a norm involving both the position and orientation. The term "position and orientation vector" as used herein may be a vector representing the position and orientation, a position vector representing only the position, or an orientation vector (quaternion) representing only the orientation.

One or two of the above three conditions may be set as conditions for update.

Figure 13:
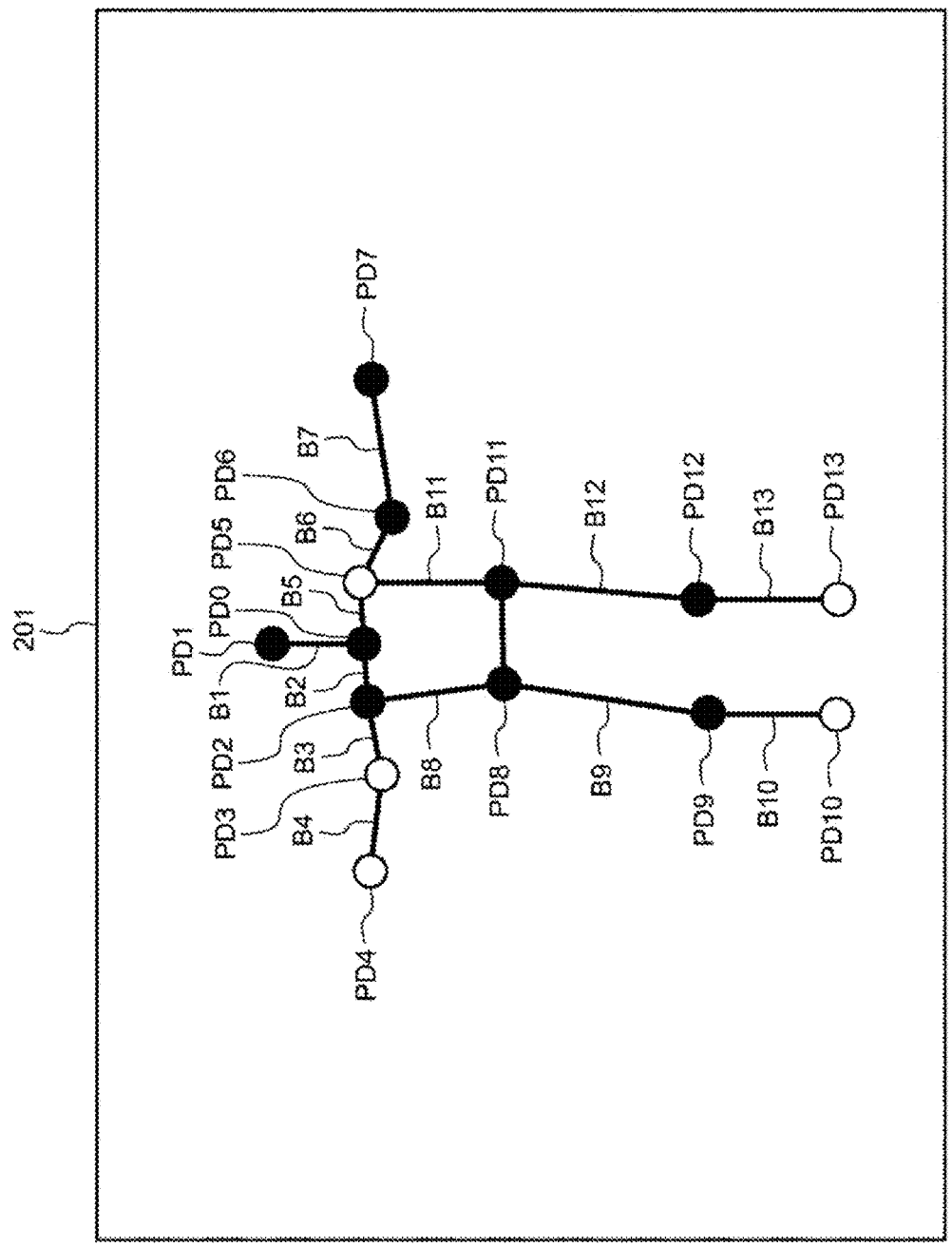
FIG. 13 is a diagram illustrating an example of measurement devices to be updated in the connection relationship image of FIG. 11.

FIG. 13 is a diagram illustrating an example of measurement devices to be updated in the connection relationship image of FIG. 11.

In FIG. 13, the measurement devices D3, D4, D5, D10, and D13 (see FIG. 6) attached at the positions PD4, PD4, PD5, PD10, and PD13 indicated by white circles are set to be updated. In the following description, the example of FIG. 13 will be referred to as appropriate.

When the measurement devices 61 to be updated are set, the pose correction processing unit 183 then focuses on measurement devices 61 to be updated that are each led to any one of the measurement devices 61 not to be updated via only one connection line. Of the measurement devices D3, D4, D5, D10, and D13 to be updated in FIG. 13, the measurement devices D3, D5, D10, and D13 have a single connection line B3, B5 (or B6 or B11), B10, and B13 leading to the measurement devices D2, D0 (or D6 or D11) D9, and D12 not to be updated, respectively. Accordingly, the pose correction processing unit 183 focuses on the measurement devices D3, D4, D5, D10, and D13 to be updated, other than the measurement device D4.

Subsequently, for each of the measurement devices 61 to be updated of interest, the pose correction processing unit 183 updates (corrects) the position and orientation (position and orientation vector) of the measurement device 61 supplied as the position and orientation data from the measurement device 61 to a value that satisfies the following Conditional Expression (16). Specifically, the estimated value of the position and orientation of the measurement device 61 of interest is corrected so that the value in the curly brackets of Expression (16) is minimized. The value of the position and orientation of the measurement device 61 after the correction (update) is referred to as the updated value.

[Math. 16]

$$\min_{p_j, \psi_{q_j}} \left\{ W_b(\|e_B\|^2) + w_c\left(\sum_{i \in C} \|e_C\|^2\right) + w_r\left(\sum_{n \in N} \|e_R\|^2\right) \right\} \quad (16)$$

In Expression (16), $e_B$ represents a difference between the estimated value of the position and orientation (position and orientation vector) supplied as the position and orientation data from the measurement device 61 of interest and the updated value of the updated position and orientation (position and orientation vector). The first term in the curly brackets of Expression (16) indicates a value obtained by multiplying the square of the norm of $e_B$ by a weight $w_b$. The weight $w_b$ is set to a larger value as the error covariance supplied as the error covariance data from the measurement device 61 of interest is smaller, for example. This ensures that the updated value of the position and orientation do not change too much from the estimated value.

Besides, $e_C$ represents a difference (reprojection error) between the position of a feature point supplied as feature point data from the measurement device 61 of interest and the position of the feature point calculated from the updated value of the position and orientation of the measurement device 61 of interest. The second term in the curly brackets of Expression (16) indicates a value obtained by multiplying a weight $w_c$ by a value obtained by adding up the square of the norm of $e_C$ for all the feature points. As the weight $w_c$, for example, the variance of the reprojection error can be used. This makes is possible to normalize and add up $e_B$ and $e_C$.

Besides, $e_R$ represents a change in distance (norm), with respect to past distance (for example, last updated), between the position and orientation of the measurement device 61 of interest (position and orientation vector representing the updated value) and the position and orientation (position and orientation vector of the estimated value) of a measurement device 61 not to be updated to which the measurement device 61 of interest is connected by a single connection line. The past distance (norm) to be referred to is not limited to the last updated distance, but may be any value based on a past norm, and the same value set and detected at initialization may be reused. Calculation of $e_R$ is represented by Equation (17).

[Math. 17]

$$e_R = |p_{j_k} - p_{n_k}| - |p_{j_{k-1}} - p_{n_{k-1}}| \quad (17)$$

Here, j represents the number of the measurement device 61 of interest, and k represents the k-th time step; n represents the number of a measurement device 61 not to be updated that is connected to the measurement device 61 of interest by a single connection line, that is, adjacent to the measurement device 61 of interest; and a capital letter P represents the updated position and orientation (position and orientation vector) of the measurement device 61 of interest, and a small letter p represents the position and orientation (position and orientation vector) of the measurement device 61 not to be updated of the number n.

The third term in the curly brackets of Expression (16) indicates a value obtained by multiplying a weight $w_r$ by a value obtained by adding up the square of the norm of $e_R$ for all the measurement devices not to be updated.

For the position and orientation of the measurement device 61 of interest, the pose correction processing unit 183 obtains the position and orientation as an updated value such that the value in the curly brackets of Expression (16) is minimized.

However, the IMU 73 has observability in the direction of gravity, but does not have observability in the direction (yaw) on a plane perpendicular to the direction of gravity. Therefore, for the position and orientation vector, the quaternion indicating the orientation is decomposed into ($\Psi$, $\varphi$, $\theta$) ($\Psi$ is yaw, $\varphi$ is pitch, $\theta$ is roll) as the corresponding orientation, and ($\varphi$, $\theta$) are fixed, to calculate an optimal updated value.

Instead of Expression (16), an expression excluding any one of the first to third terms in the curly brackets of Expression (16), or an expression with only the second or third term may be used to calculate the updated value.

Subsequently, the pose correction processing unit 183 focuses on measurement devices 61 to be updated that are each led to any one of the measurement devices 61 not to be updated via two connection lines. In FIG. 13, of the measurement devices to be updated D3, D4, D5, D10, and D13, the measurement device D4 is led to the measurement device D2 not to be updated via two connection lines B3 and B4. Accordingly, the pose correction processing unit 183 focuses on the measurement device D4 of the measurement devices D3, D4, D5, D10, and D13 to be updated. For the updated measurement devices D3, D5, D10, and D13, their positions and orientations may be used as updated values, and they may be treated as non-updated measurement devices 61 that are not to be updated.

Likewise for each of the measurement devices 61 to be updated newly focused on, the pose correction processing unit 183 updates (corrects) the position and orientation (position and orientation vector) of the measurement device 61 supplied as the position and orientation data from the measurement device 61 to a value that satisfies Expression (16). In the calculation based on Expression (16), the pose correction processing unit 183 uses the value of the position and orientation of a measurement device 61 to be updated that is led to the measurement device 61 of interest via a single connection line. As the position and orientation to be used at that time, the pose correction processing unit 183 uses the already-obtained updated value.

As described above, the pose correction processing unit 183 calculates the update value of the position and orientation in order from the measurement device to be updated that is led to the measurement device 61 not to be updated via the smallest number of connection lines, among all the measurement devices to be updated.

Then, the pose correction processing unit 183 corrects the positions and orientations of the measurement devices 61 to be updated of the positions and orientations supplied from the measurement devices 61 to the updated values, thereby generating pose data that represents the overall posture of the subject person 101. The pose correction processing unit 183 supplies the generated pose data to another processing unit and each measurement device 61.

<Procedure for Processing of Correcting (Updating) Positions and Orientations of Measurement Devices>

Figure 14:
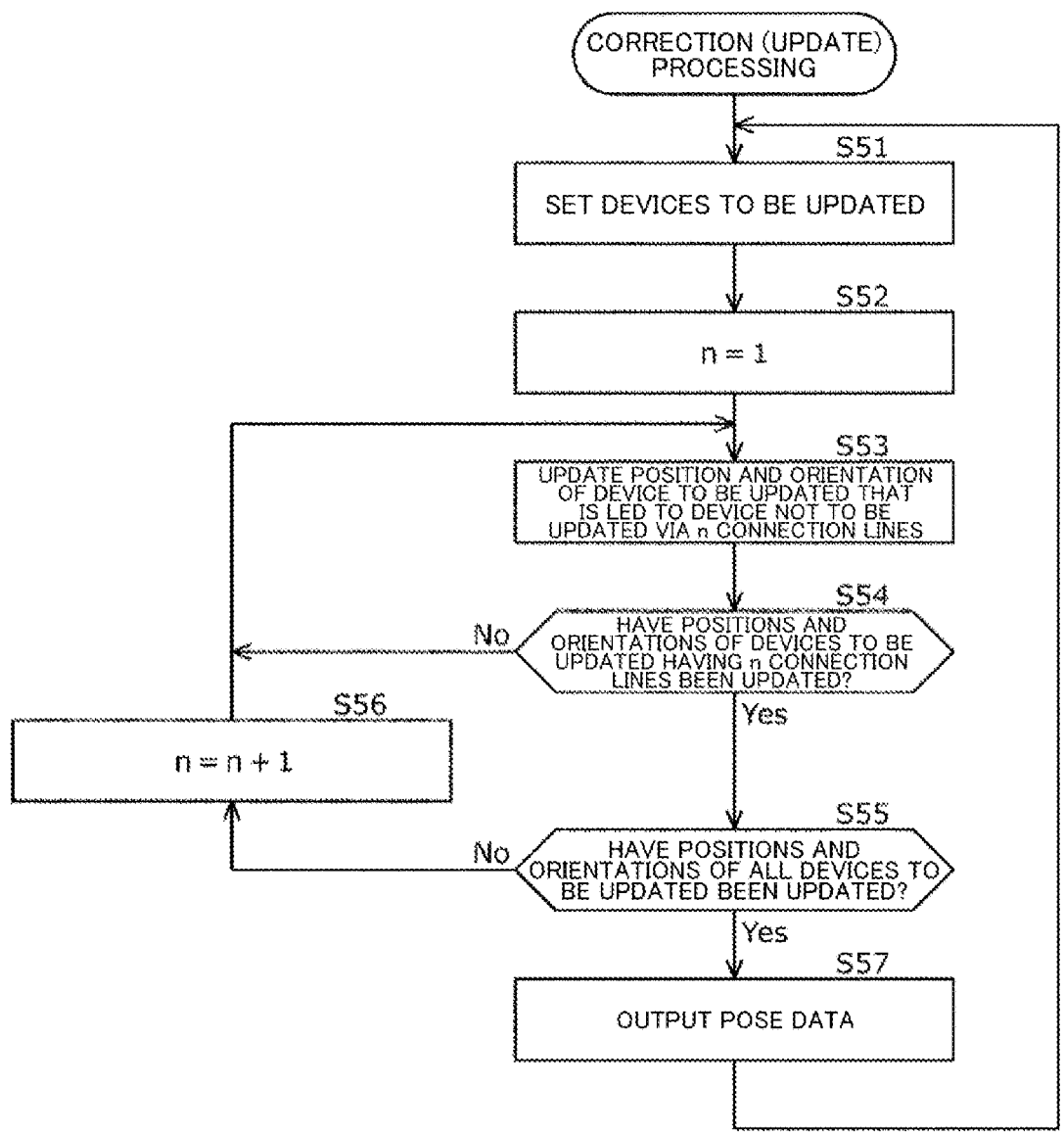
FIG. 14 is a flowchart illustrating an example of a procedure of processing of correcting positions and orientations of the measurement devices, performed by a pose correction processing unit.

FIG. 14 is a flowchart illustrating an example of a procedure of processing of correcting positions and orientations of the measurement devices 61, performed by the pose correction processing unit 183.

In FIG. 14, in step S51, the pose correction processing unit 183 sets, of the measurement devices 61 worn by the subject person, the measurement devices 61 to be updated for which the positions and orientations supplied from the measurement devices 61 are to be corrected (updated).

The pose correction processing unit 183 sets, as the measurement devices 61 to be updated, a measurement device 61 for which the error covariance is equal to or greater than a predetermined threshold value, a measurement device 61 in which the number of feature points is equal to or less than a predetermined threshold value, or if the distance between two measurement devices 61 having an adjacency relationship is equal to or greater than a predetermined threshold value, the measurement device 61 with the higher error covariance of the two measurement devices 61. The processing proceeds from step S51 to step S52. There may be a case where there is no measurement device to be updated, and in that case, the processing proceeds to step S57 without performing the update.

In step S52, a parameter n is set to 1. The processing proceeds from step S52 to step S53.

In step S53, the pose correction processing unit 183 updates, of the measurement devices to be updated, a measurement device to be updated that is led to any one of the measurement devices not to be updated via n connection lines, based on Equation (16). The processing proceeds from step S53 to step S54, if there is no measurement device to be updated having n connection lines, the processing skips steps S53 and S54 and then proceeds to step S55.

In step S54, the pose correction processing unit 183 determines whether or not the positions and orientations of all the measurement devices to be updated that are each led to any one of the measurement devices not to be updated via n connection lines have been updated.

If it is determined in step S54 that the positions and orientations of all measurement devices to be updated that is led to any one of the measurement devices not to be updated via n connection lines has not been updated, the processing is returned to step S53 and is repeated from step S53.

If it is determined in step S54 that the positions and orientations of all the measurement devices to be updated that are each led to any one of the measurement devices not to be updated via n connection lines have been updated, the processing proceeds from step S54 to step S55.

In step S55, the pose correction processing unit 183 determines whether or not the positions and orientations of all the measurement devices to be updated have been updated.

If it is determined in step S55 that the position and orientation of a measurement device to be updated that is led to any one of the measurement devices not to be updated via n connection lines has not been updated, the processing proceeds from step S55 to step S56, and then the parameter n is incremented. The processing is returned from step S56 to step S53 and is repeated from step S53.

If it is determined in step S55 that the positions and orientations of all the measurement devices to be updated have been updated, the processing proceeds to step S57.

In step S57, the pose correction processing unit 183 sets the positions and orientations of the measurement devices 61 not to be updated as the estimated values of the positions and orientations supplied from the measurement devices 61, and sets the positions and orientations of the measurement devices 61 to be updated as the updated values updated in step S53. Then, the pose correction processing unit 183 outputs to another processing unit the positions and orientations of all the measurement devices 61 as pose data that represents the posture of the subject person. After step S57, the processing is returned to step S51, and is repeated from step S51 each time new data is supplied from each measurement device 61.

As described above, according to the motion capture system 51 to which the present technology is applied, it is possible to construct an environment-independent motion capture system without the need to prepare an external environment such as a camera. Specifically, no external camera to be needed makes it possible to reduce restrictions and problems such as a restriction on the movable range due to camera placement and loss of motion data due to occlusion. In addition, it is easy to carry, so that motion capture can be performed in a relatively free location.

Moreover, the user is allowed to freely set the positional relationship of the joints, resulting in easy maintenance.

Each measurement device 61 is required only to exchange data with the information processing device 64, so that there is no need to transmit and receive data between the measurement devices 61. Accordingly, even if the number of parts to be estimated increases, it is possible to estimate the position and the like of each measurement device 61 with high accuracy without affecting the amount of calculation processing in the measurement device 61.

Moreover, when the power consumption is severe, it is also possible to operate only the IMU 73 partially, which has the effect of reducing the power consumption of the entire system.

Furthermore, the position and orientation detected by each measurement device 61 are corrected in consideration of the connection relationship with other measurement devices 61, and thus, the position and orientation of each measurement device 61 is corrected with high accuracy against reduced accuracy due to the bias (drift) of the IMU, so that the detection accuracy of the posture of the subject person (measurement target) is improved.

<Program>

The above-described image correction processing unit 81, feature point detection and tracking processing unit 82, IMU correction processing unit 83, self-position estimation processing unit 84, and initialization processing unit 85, which are included in the measurement device 61, and part or all of the above-described series of processing in the information processing device 64 can be implemented by hardware or by software. In a case in which the series of processing is performed by software, a program including the software is installed in a computer. Here, the computer includes a computer embedded in dedicated hardware or, for example, a general-purpose computer capable of executing various functions by installing various programs.

Figure 15:
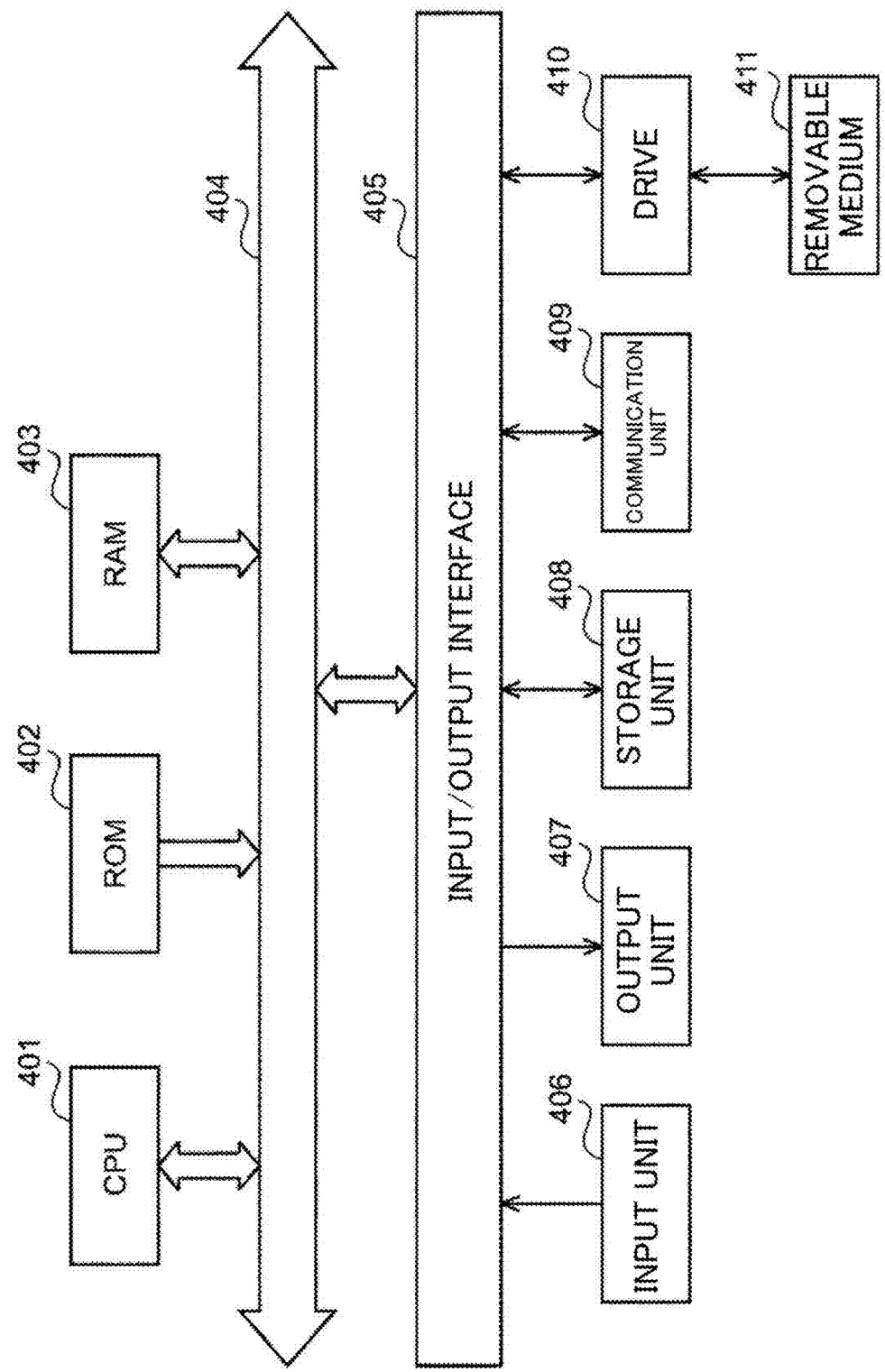
FIG. 15 is a block diagram illustrating a configuration example of hardware of a computer that executes a series of processing according to a program.

FIG. 15 is a block diagram showing a configuration example of hardware of a computer that executes the above-described series of processing according to a program.

In the computer, a central processing unit (CPU) 401, a read-only memory (ROM) 402, and a random access memory (RAM) 403 are connected to each other by a bus 404.

An input/output interface 405 is further connected to the bus 404. An input unit 406, an output unit 407, a storage unit 408, a communication unit 409, and a drive 410 are connected to the input/output interface 405.

The input unit 406 is constituted by a keyboard, a mouse, a microphone, or the like. The output unit 407 is constituted of a display, a speaker, or the like. The storage unit 408 is a hard disk, non-volatile memory, or the like. The communication unit 409 is a network interface or the like. The drive 410 drives a removable medium 411 such as a magnetic disk, an optical disc, a magneto-optical disk, or a semiconductor memory.

In the computer configured as described above, for example, the CPU 401 loads a program stored in the storage unit 408 into the RAM 403 via the input/output interface 405 and the bus 404 and executes the program to perform the above-described series of processing.

The program executed by the computer (the CPU 401) can be recorded on, for example, the removable medium 411 serving as a package medium for supply. The program can be supplied via a wired or wireless transmission medium such as a local area network, the Internet, or digital satellite broadcasting.

In the computer, by mounting the removable medium 411 on the drive 410, it is possible to install the program in the storage unit 408 via the input/output interface 405. The program can be received by the communication unit 409 via a wired or wireless transfer medium and can be installed in the storage unit 408. In addition, this program may be installed in advance in the ROM 402 or the storage unit 408.

Note that the program executed by a computer may be a program that performs processing chronologically in the order described in the present specification or may be a program that performs processing in parallel or at a necessary timing such as a called time.

The present technique can be also configured as follows:

(1)
An information processing device including a posture estimation unit that estimates a posture of a measurement; target based on a position and orientation of each of a plurality of measurement devices arranged at a plurality of parts of the measurement target and based on a connection relationship between the measurement devices that is set based on positions and orientations of the measurement devices, each measurement device including an inertial sensor.

(2)
The information processing device according to (1), wherein the posture estimation unit
sets the measurement device to be updated based on the connection relationship, and
updates the posture of the measurement target based on the position and orientation of the measurement device to be updated.

(3)
The information processing device according to (2), wherein the posture estimating unit; updates the posture of the measurement target by correcting the position and orientation of the measurement device to be updated.

(4)
The information processing device according to (2) or (3), wherein the posture estimation unit
sets as the measurement device to be updated a measurement device for which an error covariance related to the position and orientation of the measurement device is equal to or greater than a predetermined threshold value, or a measurement device in which a difference in position and orientation between the measurement device and an adjacent measurement device is equal to or greater than a predetermined threshold value.

(5)
The information processing device according to any one of (2) to (4), wherein the posture estimation unit
corrects the position and orientation of the measurement device to be updated such that a change of difference in position and orientation, with respect to a past difference, between the measurement device to be updated and a measurement device adjacent to the measurement device to be updated is reduced.

(6)
The information processing device according to (5), wherein,
in a case where there are a plurality of measurement devices adjacent to the measurement device to be updated, the posture estimation unit corrects the position and orientation of the measurement device to be updated such that a value obtained by adding up a square of the change of difference with respect to the past difference for the plurality of measurement devices adjacent to the measurement device to be updated is reduced.

(7)
The information processing device according to (5) or (6), wherein the measurement device adjacent to the measurement device to be updated is a measurement device not to be updated.

(8)
The information processing device according to any one of (4) to (7), wherein, when a difference in position and orientation between two adjacent measurement devices is equal to or greater than a predetermined threshold value, the posture estimation unit sets as the measurement device to be updated the measurement device with the higher error covariance of the two measurement devices.

(9)
The information processing device according to any one of (4) to (8), wherein, when no other measurement device is arranged at a part on a skeleton of the measurement target between two measurement devices, the posture estimation unit sets one of the two measurement devices as the adjacent measurement device.

(10)
The information processing device according to (9), wherein,
only in a case where the two measurement devices are arranged at parts of the measurement target such that a change of distance between the two measurement devices is equal to or less than a predetermined threshold value, the posture estimation unit sets one of the two measurement devices as the adjacent measurement device.

(11)
The information processing device according to any one of (4) to (10), further including a connection relationship setting unit that sets the adjacent measurement device for each of the plurality of measurement devices based on a users selection.

(12)
The information processing device according to (2), wherein the measurement device includes an image sensor, detects a feature point in an image captured by the image sensor, and outputs the position of the detected feature point.

(13)
The information processing device according to (12), wherein the posture estimation unit
sets as the measurement device to be updated a measurement device in which the number of detected feature points is equal to or less than a predetermined threshold, of the plurality of measurement devices.

(14)
The information processing device according to (12) or (13), wherein the posture estimation unit
corrects the position and orientation of the measurement device to be updated such that a difference between the position of the feature point output from the measurement device to be updated and a position of the feature point detected for the corrected position and orientation of the measurement device to be updated is reduced.

(15)
The information processing device according to (14), wherein,
when a plurality of feature points are detected by the measurement device to be updated, the posture estimation unit corrects the position and orientation of the measurement device to be updated such that a value obtained by adding up a square of the difference for the plurality of feature points is reduced.

(16)
The information processing device according to any one of (12) to (15), wherein the measurement device
estimates the position and orientation of the measurement device by a Kalman filter using the positions of the feature points detected in the image as observation values.

(17)
The information processing device according to any one of (3) to wherein the posture estimation unit
supplies the corrected position and orientation of the measurement device to be updated to the measurement device to be updated.

(18)
An information processing method including, by a posture estimation unit of
an information processing device,
estimating a posture of a measurement target based on a position and orientation of each of a plurality of measurement devices arranged at a plurality of parts of the measurement target and based on a connection relationship between the measurement devices that is set based on positions and orientations of the measurement devices, each measurement device including an inertial sensor.

(19)
A program for causing a computer to function as:
a posture estimation unit that estimates a posture of a measurement target based on a position and orientation of each of a plurality of measurement devices arranged at a plurality of parts of the measurement target and based on a connection relationship between the measurement devices that is set based on positions and orientations of the measurement devices, each measurement device including an inertial sensor.

REFERENCE SIGNS LIST

51 Motion capture system
61 Measurement device
63 Communication device
64 Information processing device
71 Image sensor
72 Logic circuit board
81 Image correction processing unit
82 Feature point detection and tracking processing unit
83 IMU correction processing unit
84 Self-position estimation processing unit
85 Initialization processing unit
171 Posture estimation unit
182 Device connection relationship determination unit
183 Pose correction processing unit

The invention claimed is:

1. An information processing device comprising:
circuitry configured to
estimate a posture of a measurement target based on a position and an orientation of each of a plurality of measurement devices arranged at a plurality of parts of the measurement target and based on a connection relationship between the plurality of measurement devices that is set based on the position and the orientation of each of the plurality of measurement devices, each measurement device including an inertial sensor,
set a measurement device to be updated based on the connection relationship, and
correct the position and the orientation of the measurement device to be updated according to a change of a difference in the position and the orientation of the measurement device to be updated, with respect to a past difference.

2. The information processing device according to claim 1, wherein the circuitry is further configured to update the posture of the measurement target based on the position and orientation of the measurement device to be updated.

3. The information processing device according to claim 2,
wherein the circuitry updates the posture of the measurement target by correcting the position and orientation of the measurement device to be updated.

4. The information processing device according to claim 2,
wherein the circuitry sets as the measurement device to be updated a measurement device for which an error covariance related to the position and the orientation of the measurement device is equal to or greater than a predetermined threshold value, or a measurement device in which the difference in the position and the orientation between the measurement device and an adjacent measurement device is equal to or greater than a predetermined threshold value.

5. The information processing device according to claim 2,
wherein the circuitry corrects the position and orientation of the measurement device to be updated such that the change of the difference in the position and the orientation is reduced, with respect to the past difference, between the measurement device to be updated and a measurement device adjacent to the measurement device to be updated.

6. The information processing device according to claim 5,
wherein, in a case where there are a plurality of measurement devices adjacent to the measurement device to be updated, the circuitry corrects the position and the orientation of the measurement device to be updated such that a value obtained by adding up a square of the change of the difference with respect to the past difference is reduced for the plurality of measurement devices adjacent to the measurement device to be updated.

7. The information processing device according to claim 5, wherein the measurement device adjacent to the measurement device to be updated is a measurement device not to be updated.

8. The information processing device according to claim 4, wherein, when the difference in the position and the orientation between two adjacent measurement devices is equal to or greater than a predetermined threshold value, the circuitry sets as the measurement device to be updated the measurement device with the higher error covariance of the two measurement devices.

9. The information processing device according to claim 4, wherein, when no other measurement device is arranged at a part on a skeleton of the measurement target between two measurement devices, the circuitry sets one of the two measurement devices as the adjacent measurement device.

10. The information processing device according to claim 9, wherein, only in a case where the two measurement devices are arranged at parts of the measurement target such that a change of distance between the two measurement devices is equal to or less than a predetermined threshold value, the circuitry sets one of the two measurement devices as the adjacent measurement device.

11. The information processing device according to claim 4, wherein the circuitry is further configured to set the adjacent measurement device for each of the plurality of measurement devices based on a selection by a user.

12. The information processing device according to claim 2, wherein each measurement device includes an image sensor configured to
    detect a feature point in an image captured by the image sensor, and
    output a position of the detected feature point.

13. The information processing device according to claim 12, wherein the circuitry sets as the measurement device to be updated a measurement device in which a number of detected feature points is equal to or less than a predetermined threshold, among the plurality of measurement devices.

14. The information processing device according to claim 12, wherein the circuitry corrects the position and orientation of the measurement device to be updated such that a difference is reduced between the position of the detected feature point output from the measurement device to be updated and a position of the feature point detected for the corrected position and the corrected orientation of the measurement device to be updated.

15. The information processing device according to claim 14, wherein, when a plurality of feature points are detected by the measurement device to be updated, the circuitry corrects the position and the orientation of the measurement device to be updated to reduce a value obtained by adding up a square of the difference for the plurality of feature points.

16. The information processing device according to claim 12, wherein the measurement device estimates the position and orientation of the measurement device by a Kalman filter using the positions of the feature points detected in the image as observation values.

17. The information processing device according to claim 3, wherein the circuitry supplies the corrected position and orientation of the measurement device to be updated to the measurement device to be updated.

18. An information processing method comprising:
    estimating a posture of a measurement target based on a position and an orientation of each of a plurality of measurement devices arranged at a plurality of parts of the measurement target and based on a connection relationship between the plurality of measurement devices that is set based on the position and the orientation of the plurality of measurement devices, each measurement device including an inertial sensor;
    setting a measurement device to be updated based on the connection relationship; and
    correcting the position and the orientation of the measurement device to be updated according to a change of a difference in the position and the orientation of the measurement device to be updated, with respect to a past difference.

19. A non-transitory computer-readable storage medium having embodied thereon a program, which when executed by a computer causes the computer to execute a method, the method comprising:
    estimating a posture of a measurement target based on a position and an orientation of each of a plurality of measurement devices arranged at a plurality of parts of the measurement target and based on a connection relationship between the plurality of measurement devices that is set based on the position and the orientation of each of the plurality of measurement devices, each measurement device including an inertial sensor;
    setting a measurement device to be updated based on the connection relationship; and
    correcting the position and the orientation of the measurement device to be updated according to a change of a difference in the position and the orientation of the measurement device to be updated, with respect to a past difference.

* * * * *